United States Patent [19]

Stephens et al.

[11] Patent Number: 5,216,173
[45] Date of Patent: Jun. 1, 1993

[54] N-CYANOIMIDES

[75] Inventors: Randall Stephens, Sebastopol; Linda A. Domeier, Windsor, both of Calif.

[73] Assignee: Henkel Research Corporation, Santa Rosa, Calif.

[21] Appl. No.: 558,028

[22] Filed: Jul. 23, 1990

Related U.S. Application Data

[63] Continuation-in-part of Ser. No. 385,135, Jul. 25, 1989, abandoned.

[51] Int. Cl.$^5$ ............... C07D 403/02; C07D 403/06; C07D 405/12; C07D 495/04
[52] U.S. Cl. .................... 548/429; 548/433; 548/455; 548/485
[58] Field of Search ............. 548/455, 429, 433, 485

[56] References Cited

U.S. PATENT DOCUMENTS

| | | | |
|---|---|---|---|
| 3,600,406 | 8/1971 | Touval | 260/346.3 |
| 4,168,364 | 9/1979 | Seltzer et al. | 528/88 |
| 4,379,728 | 4/1983 | Lin | 156/307.3 |
| 4,384,084 | 5/1983 | Lohse et al. | 525/504 |
| 4,435,549 | 3/1984 | Lin | 525/504 |
| 4,618,712 | 10/1986 | Stockinger et al. | 564/103 |
| 4,640,944 | 2/1987 | Brooks | 523/205 |
| 4,657,987 | 4/1987 | Rock et al. | 525/432 |
| 4,859,761 | 8/1989 | Flury et al. | 525/504 |

FOREIGN PATENT DOCUMENTS

| | | |
|---|---|---|
| 0311374 | 4/1989 | European Pat. Off. . |
| 2356368 | 5/1975 | Fed. Rep. of Germany . |
| 1-238576 | 9/1989 | Japan . |

OTHER PUBLICATIONS

Zh. Org. Khim., 13(5), 968 (1977), Chemical Abstracts 87:68071n.
Encylopedia of Polymer Science and Engineering, vol. 12, pp. 364–383, 2nd Ed.

Primary Examiner—David B. Springer
Attorney, Agent, or Firm—Wayne C. Jaeschke; John E. Drach; Henry E. Millson, Jr.

[57] ABSTRACT

Polyfunctional N-cyanoimides and their precursors and derivatives are disclosed along with methods for their preparation and interconversion. Also disclosed are curable compositions comprising the N-cyanoimides or poly(amide-cyanoamides) and reactive diluents as well as novel dianhydrides, polyimides, and poly(amide-cyanoamides) and methods for making them.

21 Claims, No Drawings

N-CYANOIMIDES

CROSS-REFERENCE TO RELATED APPLICATIONS

This is a continuation-in-part of application Ser. No. 07/385,135, filed on Jul. 25, 1989, now abandoned the entire contents of which are incorporated herein by reference.

BACKGROUND OF THE INVENTION

1. Field of the Invention

This invention relates to poly-N-cyanoimides which are useful as monomers for synthesizing polyimides and a process for preparing the N-cyanoimides. This invention also relates to a process for preparing polyimides, a process for curing epoxy resins, epoxy resin-cyanoimide compositions, reactive diluent-cyanoimide-amine compositions, poly(amide-cyanoamide) compositions, reactive diluentpoly(amide-cyanoamide) compositions, epoxy resin-polyimide compositions, bis-cycloalkyl dianhydrides, a process for preparing bis-cycloalkyl dianhydrides, and bis-cycloalkyl dianhydride based polyimides.

2. Description of the Related Art

Polymers containing imide groups are widely recognized and utilized for their heat resistant properties. Imide groups have been incorporated into linear thermoplastics, into oligomers end-capped with reactive groups such as acetylene or nadimide, and into crosslinkable thermoset monomers such as bismaleimides. Commercial imide polymers are available, for example, in the form of high $T_g$ thermoplastics, as solutions of the precursor poly(amide-acid), as reactive oligomers, as solutions of the amine and ester-acid precursors which are processed in-situ to a crosslinked polyimide oligomer, and as low molecular weight bismaleimide thermoset monomers. They have been utilized as resins for fiber-reinforced composites, as engineering thermoplastics, as coatings, as adhesives, and in other applications requiring high temperature stability.

Polyimides are generally formed from the appropriate anhydride and amine precursors via a two-step reaction sequence which involves ring opening addition of the amine to the anhydride to form an amide-acid followed by either thermal or chemical dehydration and ring closure to form the imide and remove an equivalent of water. The first step in this sequence is a facile reaction which occurs readily even at room temperature while the second step requires more rigorous conditions to force the elimination of water. In some cases the anhydride may also be replaced with the corresponding ester-acid.

If the final cyclization/dehydration step is performed prior to fabrication of the desired composite, adhesive bond or other application, the resulting imide polymer is often characterized by poor solubility and/or high melt-processing temperatures. If this dehydration step is carried out as a curing process during product fabrication, the water produced by cyclization must be carefully removed to eliminate voids or other defects in the final product. Such processing and curing requires high temperatures and/or vacuum plus extended time periods, all of which add to the cost of reliably producing polyimide-based products. Furthermore, while reactive end-capped polyimide oligomers or higher molecular weight poly(amide-acids) tend to be more soluble than the corresponding high molecular weight polyimides and are therefore more readily processed as solutions, this carrier solvent must also be removed at some point in the fabrication process. Thus, most of the polyimide systems now in use require the removal during processing of either solvent or water, or both.

All these problems arise from the high $T_g$ values and low solubilities of most imide containing polymers, the very features which, in turn, make polyimides attractive. The commercial systems now in use have all evolved as particular solutions to this problem of combining outstanding final physical properties with acceptable processing requirements.

N-cyanoimides in general and poly-N-cyanoimides in particular have been found to function as "anhydride equivalents" in imide forming reactions and to provide significant advantages over the anhydrides and other precursors currently used. In particular, the temperatures required for final ring closure to the imide are lower and the by-product in this case is a non-volatile solid. The most advantageous application of the use of poly-N-cyanoimides in the preparation of polyimides is thus in those cases where the polyimide is formed during final part fabrication and where the use of N-cyanoimides can eliminate the need to remove water from the final product.

Polyfunctional N-cyanoimides are unknown in the prior art. However, certain monofunctional N-cyanoimides have been prepared. For example, diacetylcyanamide (N-cyanodiacetamide) [J. Prakt. Chem., 17(2), 14, (1875)]; bis-(4-hydroxy-3,6-dioxohexahydropyridazinyl-(4)-acetylcyanamide (German patent No. 2,356,368); N-cyanosuccinimide [J. Prakt. Chem., 22(2), 193 (1880)]; N-cyanophthalimide, 4-nitro-N-cyanophthalimide [Zh. Org. Khim., 13(5), 968 (1977), Chemical Abstracts 87: 68071n] have been prepared. None of the methods used to make the preceding compounds uses the process of the present invention or discloses the polyfunctional N-cyanoimides.

The polymeric intermediates obtained by reaction of a bis-N-cyanoimide and a diamine to form a poly(amide-cyanoamide) are unknown in the prior art. These polymeric compositions are analogous to the known poly(amide-acid) intermediates, but may be converted to the polyimide with the elimination of cyanamide instead of water. The process for converting poly(amide-cyanoamides) to polyimides is also unknown in the prior art.

The use of mono- or polyfunctional N-cyanoamides to cure epoxy resins is unknown in the prior art. Curable compositions comprising an epoxy resin and a mono- or polyfunctional N-cyanoimide are unknown despite the long history of dicyandiamide and other cyanamide derivatives as epoxy curing agents.

The use of other derivatives of cyanamide, or its dimer, as curing or hardening agents for epoxy resins is known in the art. U.S. Pat. No. 4,168,364 teaches cyanamides of organic primary amines as epoxy curing agents. U.S. Pat. Nos. 4,379,728 and 4,384,084 teach the uses of N-cyanourea compounds and cyanolactams respectively. Curable compositions containing N-cyanoamides and polyepoxy resins have been described in both U.S. Pat. Nos. 4,435,549 and 4,618,712. U.S. Pat. No. 4,859,761 discloses epoxy resin compositions containing specific cyanoguanidines as latent hardeners.

Also unknown are curable compositions comprising a reactive diluent such as an epoxy resin plus a bis-N-cyanoimide and a diamine and curable compositions comprising a reactive diluent and a poly(amide-cyanoamide).

N-Cyanoimides derived from bis-cycloalkyl dianhydrides are especially effective in certain embodiments of this invention. The bis-cyclohexyl dianhydrides of this invention are also unknown in the prior art as are the polyimides derived from them. Processes for the preparation of the bis-cycloalkyl dianhydrides have also been described only partially in the prior art.

European Patent Application 0 311 374 teaches that dicyclohexyl-3,4,3',4'-tetracarboxylic acid can be made by hydrogenating biphenyl-3,4,3',4'-tetracarboxylic acid tetramethyl ester in a solvent such as methanol, methyl acetate, tetrahydrofuran, diethyl ether, or n-hexane in the presence of a rhodium catalyst at a temperature of from 50° C. to 150° C. at a hydrogen pressure of from 2 to 100 atmospheres followed by hydrolysis of the reduced esters to the tetracarboxylic acid under well known acid or alkaline conditions. The patent application also teaches that the corresponding dicyclohexyl-3,4,3,4'-tetracarboxylic dianhydride can be made by dehydrating the dicyclohexyl-3,4,3',4'-tetracarboxylic acid by either heating the acid to 180° C. to 220° C. under a pressure of 30 to 100 mm Hg for 1 to 5 hours or refluxing the acid with acetic anhydride.

European Patent Application 0 311 374 also teaches polyimides having the following repeat unit

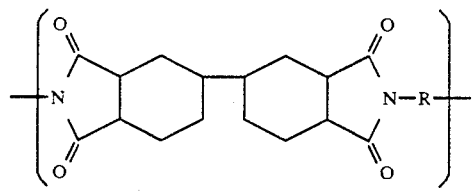

wherein R is a bivalent group can be made by reacting dicyclohexyl-3,4,3,4'-tetracarboxylic dianhydride with a diamine to produce a poly(amide-acid) and dehydrating the poly(amide-acid). U.S. Pat. No. 3,600,406 teaches that bis(4-cyclohexyl-1,2-dicarboxylic anhydride) ketone can be made by hydrocarboxylation of 4-cyclohexene-1,2-diethyl carboxylate with nickel carbonyl or carbon monoxide followed by hydrolysis to the tetracarboxylic acid ketone and subsequent dehydration with acetic anhydride.

Japanese patent number 01,238,576 teaches that bis(1,2-cyclohexyldicarboxylic dianhydride) tetradecene can be made by reacting tetrahydrophthalic anhydride and 1,13-tetradecadiene at 200° C. in a nitrogen atmosphere.

SUMMARY OF THE INVENTION

The present invention provides poly-N-cyanoimides of the formula I wherein R is a polyvalent aliphatic, substituted aliphatic, aromatic, or substituted aromatic radical and n is an integer having a value of 2 or greater.

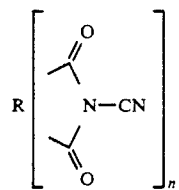

The present invention also provides a process for preparing an N-cyanoimide which comprises reacting an imide with cyanogen halide in the presence of a base to form an N-cyanoimide and isolating the N-cyanoimide. The poly-N-cyanoimides of the present invention are useful as monomers which can be polymerized with diamines to form polyimides at relatively low reaction temperatures and with the formation of cyanamide, a non-volatile solid reaction by-product.

The present invention also provides a process for making a polyimide which comprises reacting a compound having at least two primary amine functionalities and a compound of the formula I

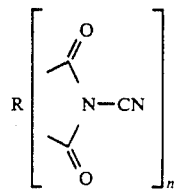

wherein R is a polyvalent aliphatic, substituted aliphatic, aromatic, or substituted aromatic radical and n is an integer having a value of 2 or greater.

The present invention further provides a process for making an N-substituted imide which comprises reacting a primary amine with a compound of the formula I

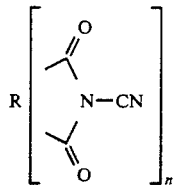

wherein R is a polyvalent aliphatic, substituted aliphatic, aromatic, or substituted aromatic radical and n is an integer having a value of 1 or greater.

In addition, the present invention provides a composition comprising an epoxy resin having at least 2 epoxide functionalities and a compound of the formula I

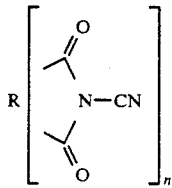

wherein R is a polyvalent aliphatic, substituted aliphatic, aromatic, or substituted aromatic radical and n is an integer having a value of 1 or greater.

The present invention also provides a process for curing an epoxy resin which comprises reacting an epoxy resin with a compound of the formula I

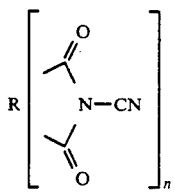

wherein R is a polyvalent aliphatic, substituted aliphatic, aromatic, or substituted aromatic radical and n is an integer having a value of 1 or greater at a temperature of at least 25° C.

A composition is also provided which comprises a compound having at least two primary amine functionalities, a compound of the formula I

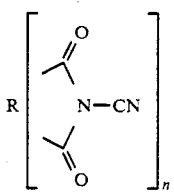

wherein R is a polyvalent aliphatic, substituted aliphatic, aromatic, or substituted aromatic radical and n is an integer having a value of 2 or greater, and a reactive diluent. The cured or partially cured reaction products of this composition are also provided. These compositions are useful as adhesives or matrix resins.

A compound of the formula II is provided

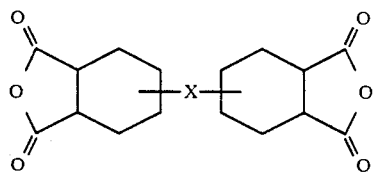

wherein X is O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 and R$^1$ through R$^6$ are independently hydrogen or an aliphatic or aromatic radical. These dianhydrides are useful as monomers which can be polymerized with diamines to form polyimides or as precursors for poly N-cyanoimides.

A process for making a compound of formula II is also provided

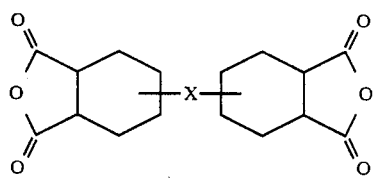

wherein X is O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 and R$^1$ through R$^6$ are independently hydrogen or an aliphatic or aromatic radical, comprising the steps of: (1) hydrogenating a compound of the formula III

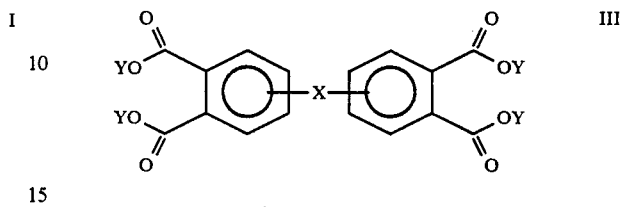

wherein X is O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 and R$^1$ through R$^6$ are independently hydrogen or an aliphatic or aromatic radical and Y is an aliphatic or aromatic radical in the presence of a catalyst effective amount of a noble metal catalyst to form a reduced reaction product; (2) hydrolyzing said reduced reaction product to form a reduced tetracarboxylic acid; and (3) dehydrating said reduced tetracarboxylic acid.

The present invention also provides a polyimide of the formula IV

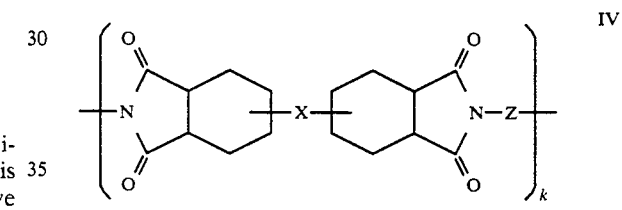

wherein X is O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 and R$^1$ through R$^6$ are independently hydrogen or an aliphatic or aromatic radical and Y is an aliphatic or aromatic radical and Z is one or more substituted or unsubstituted divalent carbocyclic or heterocyclic rings, a divalent moiety containing two benzylic sites such as p-xylenediylidene or p-bitoluenediylidene, or a divalent aliphatic radical wherein the atom γ to the imide nitrogen is a saturated carbon atom or a nitrogen, oxygen or divalent sulfur atom and K is an integer having a value of at least 2.

A poly(amide-cyanoamide) of the formula V is also provided

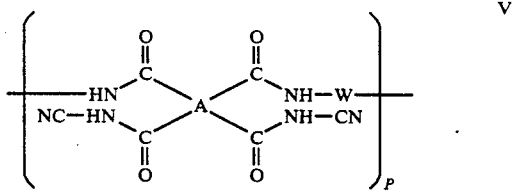

wherein A is a tetravalent aliphatic, substituted aliphatic, aromatic, or substituted aromatic radical, W is a divalent aliphatic, substituted aliphatic, aromatic, or substituted aromatic radical, and p is an integer having a value of at least 2. This polymer is useful as a polyimide precursor.

A process for making a polyimide comprised a heating a poly(amide-cyanoamide) of the formula V is also provided

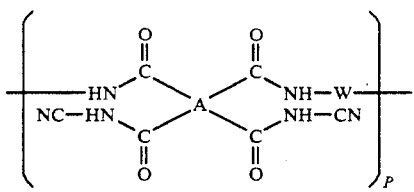
(V)

wherein A is a tetravalent aliphatic, substituted aliphatic, aromatic, or substituted aromatic radical, W is a divalent aliphatic, substituted aliphatic, aromatic, or substituted aromatic radical, and p is an integer having a value of at least 2 to a temperature sufficient to effect ring closure and elimination of cyanamide.

Further provided is a composition comprising a poly(amide-cyanoamide) of the formula V plus a reactive diluent and also the cured reaction product of that composition.

A compound of the formula VI is also provided

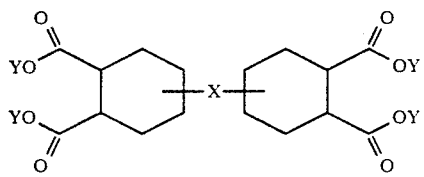
(VI)

wherein X is O, $NR^1$, $C(CF_3)_2$, $C(CH_3)_2$, CONH, COO, $(CH_2)_m$, $CR^2R^3$, $CH(OR^4)$, $C(OR^5)(OR^6)$ and wherein m is an integer having a value of at least 1 and $R^1$ through $R^6$ are independently hydrogen or an aliphatic or aromatic radical. These compounds are useful as anhydride precursors.

DESCRIPTION OF THE PREFERRED EMBODIMENTS

One group of compounds according to the present invention are poly-N-cyanoimides of the formula I wherein R is a polyvalent aliphatic, substituted aliphatic, aromatic, or substituted aromatic radical. A polyvalent aliphatic radical is any alkyl, cycloalkyl, alkenyl, cycloalkenyl, alkynyl, or cycloalkynyl radical having a valence of 4 or more. A substituted polyvalent aliphatic radical is any alkyl, cycloalkyl, alkenyl, cycloalkenyl, alkynyl, or cycloalkynyl radical having a valence of 4 or more and wherein one or more hydrogen atoms is replaced by an atom or a group of atoms other than hydrogen. A polyvalent aromatic radical is any benzenoid or non-benzenoid aromatic radical having a valence of 2 or more. A non-benzenoid aromatic radical includes carbocyclic and heterocyclic aromatic radicals. A substituted polyvalent aromatic radical is any benzenoid or non-benzenoid aromatic radical having a valence of 4 or more wherein one or more hydrogen atoms is replaced by an atom or a group of atoms other than hydrogen. The definition of a substituted polyvalent aromatic radical includes those radicals which contain aliphatic moieties and/or hetero atoms as exemplified in the following structures:

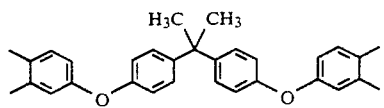

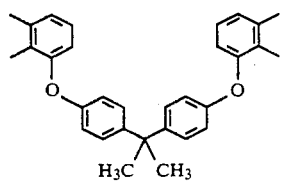

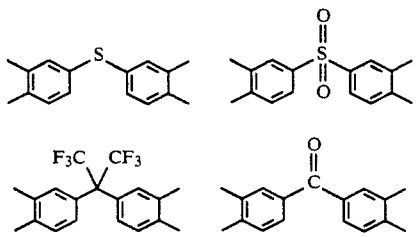

The definition of a substituted polyvalent aliphatic radical includes these radicals which contain aromatic moieties and/or hetero atoms as exemplified in the following structures:

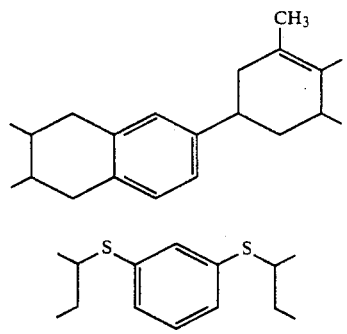

The definition of a substituted polyvalent aliphatic radical also includes those radicals shown in the following structure:

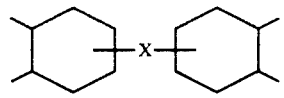

wherein X is a direct bond, O, $NR^1$, $C(CF_3)_2$, $C(CH_3)_2$, CONH, COO, $(CH_2)_m$, $CR^2R^3$, $CH(OR^4)$, $C(OR^5)(OR^6)$ and wherein m is an integer having a value of at least 1 and $R^1$ through $R^6$ are independently hydrogen or an aliphatic or aromatic radical.

In the context of the present invention, a polyvalent aliphatic radical also includes the repeat unit of a polymer. For example, in a N-cyanomaleimide polymer, the polyvalent aliphatic radical R is the ethanediylidene radical

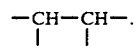

In the preceding example, the integer n in formula I would have a value equal to the number of N-cyanomaleimide units in the polymer.

The poly-N-cyanoimides of the present invention can be reacted with diamines to form polyimides. Polyimides are important commercial and industrial materials which exhibit excellent thermal and oxidative stability. They are used as replacement materials for metals and glass in high performance applications in the electronics, automotive, and aerospace industries (Encyclopedia of Polymer Science and Engineering, Volume 12, pp 364–383).

The poly-N-cyanoimides according to the present invention can be made by reacting a polyfunctional anhydride with ammonia to form the corresponding half amide-half acid, hereafter referred to as an amide-acid, followed by dehydration of the amide-acid to the corresponding cyclic imide. Other routes to polyfunctional imides may also be utilized. The cyclic imide can then be reacted with cyanogen halide in the process of the present invention to form a poly-N-cyanoimide since the process of this invention can be used to prepare any N-cyanoimide or poly-N-cyanoimide.

A polyfunctional anhydride is a compound that contains at least two cyclic carboxylic acid anhydride moieties. Cyclic carboxylic acid anhydrides are well known to those skilled in the art as anhydrides formed from vicinal dicarboxylic acids to give five- or six-membered rings. Examples of carboxylic acid anhydrides include such simple anhydrides as succinic anhydride, maleic anhydride, and phthalic anhydride. These anhydrides can be formed from succinic, maleic, and phthalic acids respectively, usually by heating the acids to temperatures of from about 200° C. to about 300° C. to eliminate water between the two vicinal carboxyl groups.

Any polyfunctional anhydride can be used to make the compounds of the present invention. Examples of such polyfunctional anhydrides include but are not limited to the following dianhydrides and their derivatives:

pyromellitic dianhydride;
3,3',4,4'-benzophenone tetracarboxylic dianhydride;
2,3,4,5-pyrrolidine tetracarboxylic dianhydride;
3,4,9,10-perylene tetracarboxylic dianhydride;
2,3,6,7-naphthalene tetracarboxylic dianhydride;
1,2,5,6-naphthalene tetracarboxylic dianhydride;
1,4,5,8-naphthalene tetracarboxylic dianhydride;
3,3',4,4'-diphenyl tetracarboxylic dianhydride;
2,2',3,3'-diphenyl tetracarboxylic dianhydride;
3,3',4,4'-diphenyl ether tetracarboxylic dianhydride;
3,3',4,4'-diphenyl sulfide tetracarboxylic dianhydride;
3,3',4,4'-diphenyl sulfone tetracarboxylic dianhydride;
3,3',4,4'-diphenylmethane tetracarboxylic dianhydride;
2,2-bis(3,4-dicarboxyphenyl) propane dianhydride;
2,2-bis(2,3-dicarboxyphenyl) propane dianhydride;
2,2-bis(3,4-dicarboxyphenyl)-hexafluoropropane dianhydride;
2,2-bis(2,3-dicarboxyphenyl)-hexafluoropropane dianhydride;
1,3-bis(3,4-dicarboxyphenyl)benzene dianhydride;
1,3-bis(2,3-dicarboxyphenyl)benzene dianhydride;
1,4-bis(3,4-dicarboxyphenyl)benzene dianhydride;
1,4-bis(2,3-dicarboxyphenyl)benzene dianhydride;
4,4'-bis(3,4-dicarboxyphenyl)biphenyl dianhydride;
4,4'-bis(2,3-dicarboxyphenyl)biphenyl dianhydride;
4,4'-bis(3,4-dicarboxyphenyl)diphenyl ether dianhydride;
4,4'-bis(2,3-dicarboxyphenyl)diphenyl ether dianhydride;
4,4'-bis(3,4-dicarboxyphenyl)diphenyl sulfide dianhydride;
4,4'-bis(2,3-dicarboxyphenyl)diphenyl sulfide dianhydride;
4,4'-bis(3,4-dicarboxyphenyl)diphenyl sulfone dianhydride;
4,4'-bis(2,3-dicarboxyphenyl)diphenyl sulfone dianhydride;
4,4'-bis(3,4-dicarboxyphenyl)diphenylmethane dianhydride;
4,4'-bis(2,3-dicarboxyphenyl)diphenylmethane dianhydride;
4,4'-bis(3,4-dicarboxyphenyl)benzophenone dianhydride;
4,4'-bis(2,3-dicarboxyphenyl)benzophenone dianhydride;
2,2-bis[4-(3,4-dicarboxyphenoxy)phenyl]-propane dianhydride;
2,2-bis[4-(2,3-dicarboxyphenoxy)phenyl]propane dianhydride;
2,2-bis[4-(3,4-dicarboxyphenoxy)phenyl]hexafluoropropane dianhydride;
2,2-bis[4-(2,3-dicarboxyphenoxy)phenyl]hexafluoropropane dianhydride;
5-[2,5-dioxotetrahydro-3-furanyl]-3-cyclohexene-1,2-dicarboxylic anhydride;
ethylenetetracarboxylic dianhydride;
1,2,3,4-cyclopentanetetracarboxylic dianhydride;
1,2,3,4-cyclobutanetetracarboxylic dianhydride;
1,3-dimethyl-1,2,3,4-cyclobutanetetracarboxylic dianhydride;
1,2,3,4-tetramethyl-1,2,3,4-cyclobutanetetracarboxylic dianhydride;
3,6-ethenohexahydropyromellitic dianhydride;
tricyclo[6.4.0.0$^{2,7}$]dodecane-1,8,4,5-tetracarboxylic dianhydride;
-tricyclo[6.4.0.0$^{2,7}$]dodecane-3,6-diphenyl-1,8,4,5-tetracarboxylic dianhydride;
tricyclo[4.2.2.0$^{2,5}$]dec-7-ene-3,4,9,10-tetracarboxylic dianhydride;

Other dianhydrides suitable for use as poly-N-cyanoimide precursors are described in U.S. Pat. No. 4,657,987 (derivatives of nitro or halo substituted phthalic anhydride) and U.S. Pat. No. 4,640,944 (derivatives of trimellitic anhydride). Also included are the cycloaliphatic equivalents of the aromatic anhydrides described above in which one or more of the aromatic rings have been hydrogenated.

Higher functionality polyanhydrides are also suitable as poly-N-cyanoimide precursors, either alone or in combination with difunctional anhydrides. Examples of such anhydrides are hexaazatriphenylene trianhydride and derivatives of phthalic anhydride such as 1,1,1-tris[4-(3,4-dicarboxyphenoxy)phenyl]-ethane trianhydride.

Other polyfunctional anhydrides which can be used to make the compounds of the present invention include any polymer having pendant anhydride functionalities. Examples of such polymers include but are not limited to maleic anhydride homopolymers, maleic anhydride copolymers such as styrenemaleic anhydride, ethylene-maleic anhydride, 1-octadecene-maleic anhydride, isobutylene-maleic anhydride, butadiene-maleic anhydride, vinyl acetate-maleic anhydride, N-vinylpyrrolidinone-maleic anhydride, methyl vinyl ether-maleic anhydride, acrylic ester-maleic anhydride, acrylic acid-maleic anhydride, acrylamide-maleic anhydride, methacrylic ester-maleic anhydride, methacrylic acid-maliec anhydride, methacrylamide-maleic anhydride and the like.

Blends of any or all the above anhydrides are also suitable as poly-N-cyanoimide precursors.

The preferred polyfunctional anhydrides are pyromellitic dianhydride; 3,3′,4,4′-benzophenone tetracarboxylic dianhydride; 3,3′4,4′-diphenyl ether detracarboxylic dianhydride; 2,2-bis(3,4-dicarboxyphenyl)hexafluoropropane dianhydride; 2,2-bis[4-(3,4-dicarboxyphenoxy)phenyl]propane dianhydride; 2,2-bis[4-(2,3-dicarboxyphenoxy)phenyl]propane dianhydride; 5-[2,5-dioxotetrahydro3-furanyl]-3-cyclohexene-1,2-dicarboxylicanhydride and isomers derived therefrom; ethylenetetracarboxylic dianhydride; 1,2,3,4-cyclopentanetetracarboxylic dianhydride; and 1,2,3,4-cyclobutanetetracarboxylic dianhydride.

Further preferred polyfunctional dianhydrides are the bis-cyclohexyl dianhydrides of formula II

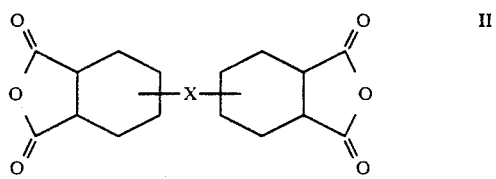

wherein X is a direct bond, O, $NR^1$, $C(CF_3)_2$, $C(CH_3)_2$, CONH, COO, $(CH_2)_m$, $CR^2R^3$, $CH(OR^4)$, $C(OR^5)(OR^6)$ and wherein m is an integer having a value of at least 1 and $R^1$ through $R^6$ are independently hydrogen or an aliphatic or aromatic radical.

In one preferred embodiment, the poly-N-cyanoimide compounds of the present invention are made by first preparing the corresponding unsubstituted imide by standard methods known in the art. Most preferably, the polyfunctional anhydride is reacted with aqueous ammonium hydroxide and the resulting ammonium salt of the amide-acid is then heated to a temperature $>100°$ C. to form the corresponding polyfunctional imide by dehydration. The polyfunctional imide is then mixed with a stoichiometric amount or slight excess of cyanogen chloride or bromide in acetone or blends of acetone with dimethylsulfoxide. Approximately an equimolar (relative to the cyanogen bromide) amount of triethylamine is then added dropwise while maintaining the reaction mixture temperature at about 0° C. After addition of the tertiary amine is complete, the reaction mixture is stirred for about 15 minutes and warmed to room temperature. The product poly-N-cyanoimide is recovered by removing the tertiary amine hydrohalide salt via filtration and/or an aqueous wash, removing the excess cyanogen halide or its adduct with the tertiary amine via an aqueous wash, and removing the reaction solvent(s) via precipitation of the N-cyanoimide product and drying or by stripping the solvent(s).

Any cyanogen halide can be used to make the compounds of the present invention. Examples of suitable cyanogen halides include but are not limited to cyanogen chloride and cyanogen bromide. The preferred cyanogen halides are cyanogen chloride and cyanogen bromide. Typically, the cyanogen halide is used in molar quantities equal to or slightly greater than the molar amounts of imide present.

Any of the commonly available inert solvents in which the imide or polyimide precursor is soluble or partially soluble can be used to make the compounds of the present invention. The preferred solvent is acetone or blends of acetone with dimethylsulfoxide.

The basic compounds which are useful in preparing the poly-N-cyanoimides according to the present invention are tertiary amines and, most preferably, triethylamine. Typically the triethylamine is used in molar quantities equal to or slightly greater than the amount of cyanogen halide used.

The preferred poly-N-cyanoimides are

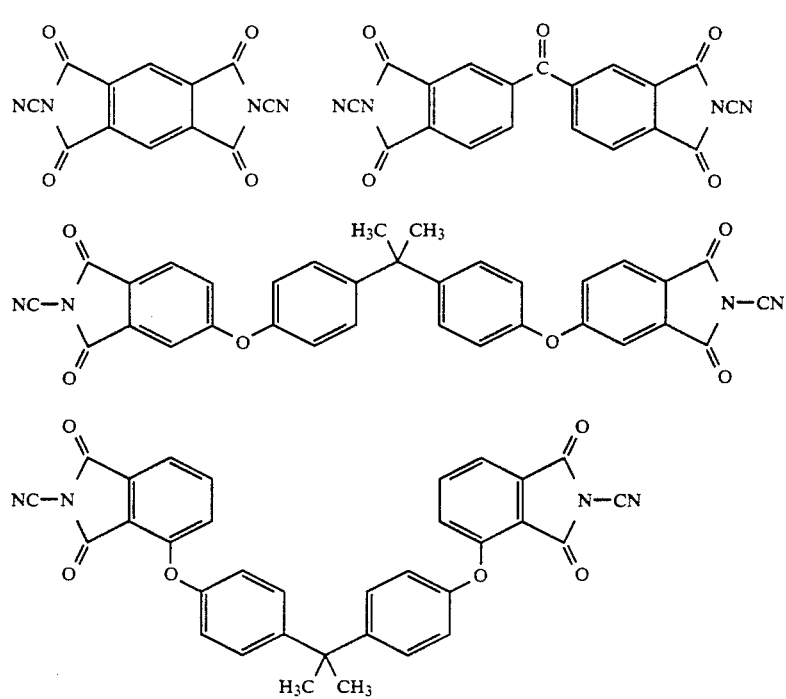

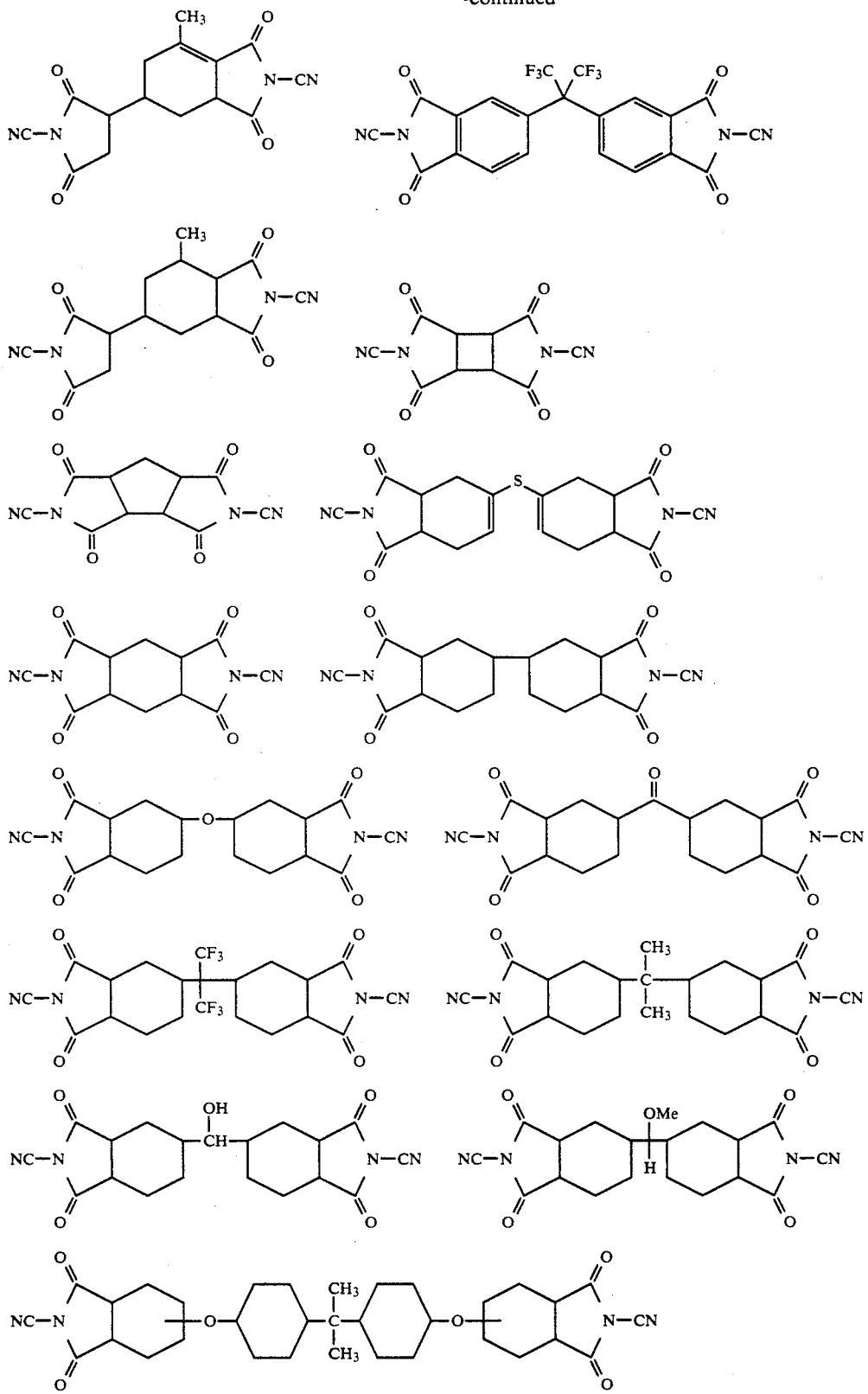

The process of making polyfunctional N-cyanoimides can be used to prepare any type of N-cyanoimide including linear and cyclic N-cyanoimides and including mono- and poly-functional N-cyanoimides. A linear N-cyanoimide is one in which the terminal carbon atoms are not joined such as N-cyanodiacetamide, $(CH_3CO)_2N-CN$, which can be made from acetic anhydride according to the process of the present invention. Other more complex linear N-cyanoimides can also be made by the process of the present invention. For example, N-cyano-N-acetylbenzamide,

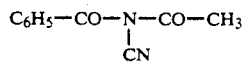

and other unsymmetrical linear N-cyanoimides can also be made by the process of the present invention. A cyclic N-cyanoimide is one in which the terminal carbon atoms are joined. N-cyanosuccinimide, N-cyanomaleimide, and N-cyanophthalimide are examples of cyclic N-cyanoimides.

In a preferred method of carrying out the process of making a poly-N-cyanoimide, a carboxylic acid anhydride is first converted to the corresponding imide by any standard method for preparing imides known in the art. Linear imides may be made by any method known in the art such as the addition of a carboxylic acid to a nitrile, or the acylation of an amide by an acyl halide, ester, or carboxylic acid. Cyclic imides can be made by reacting a cyclic carboxylic acid anhydride with ammonia to form the corresponding ammonium salt of the amide-acid. The ammonium salt of the amide-acid is then heated to a temperature $>100°$ C. to form the corresponding cyclic imide by dehydration. The linear or cyclic imide is then mixed with a stoichiometric amount or slight excess of the cyanogen halide in any inert organic solvent or solvent mixture in which the imide precursor can be wholly or partially dissolved. The imide-cyanogen halide mixture is then stirred and cooled to a temperature of about $-25°$ C. to $+10°$ C. The preferred solvents are acetone or blends of acetone with dimethylsulfoxide. The preferred temperature is $0°$ C. Approximately an equimolar (relative to the cyanogen bromide) amount of a base, preferably a tertiary amine, is then added over a period of time such that the temperature of the reaction does not exceed about $50°$ C. and preferably does not exceed about $25°$ C. The most preferred base is triethylamine. After addition of the tertiary amine is complete, the reaction mixture is allowed to warm to about $25°$ C. and is stirred at that temperature for about 15 minutes to an hour. While the method of recovering the product can vary, the preferred method involves the removal of the tertiary amine hydrohalide salt via filtration and/or an aqueous wash, the removal of excess cyanogen halide or its adduct with the tertiary amine via an aqueous wash, and the removal of the reaction solvent(s) via precipitation of the N-cyanoimide product and drying or by simple stripping of the solvent(s).

N-substituted imides can be made by reacting compounds of formula I with monofunctional primary amines. The reaction is preferably carried out by adding an amine solution to an N-cyanoimide of formula I dissolved in an inert solvent such as tetrahydrofuran (THF), dimethyl sulfoxide (DMSO), N-methylpyrrolidinone (NMP), acetone, methylene chloride, ethyl acetate, dimethylformamide (DMF), and dimethylacetamide (DMAC). The reaction mixture is then stirred for a time and temperature sufficient to form the maximum yield of product. For example, if the reaction is carried out at $50°$ C. a time period of about 30 minutes is required for the maximum yield of N-substituted imide product to form. The progress of the reaction can be monitored by gas chromatographic analysis of the reaction mixture in which the disappearance of one or both reactants is followed. In a preferred embodiment, to an approximately 10% solution of an aromatic N-cyanoimide in an inert solvent is added an approximately 30% solution of a monofunctional amine. Within 30 minutes, all of the amine is consumed, as determined by GC. The solution is then warmed to $50°$ C. and allowed to stir overnight. The product precipitates and is isolated by any method known to those skilled in the art such as by filtration.

The process of making an N-substituted imide can be used in cases where the N-cyanoimide is monofunctional and the amine is polyfunctional, or where the N-cyanoimide is polyfunctional and the amine is monofunctional, or where both the amine and the N-cyanoimide are both monofunctional.

Polyimides can be made by reacting polyfunctional N-cyanoimides (compounds of formula wherein $n>1$) and compounds having at least two primary amine functionalities. The polymerization reaction is carried out by reacting a polyfunctional N-cyanoimide and a polyfunctional amine for a sufficient time and temperature to obtain the maximum yield of product. It will be apparent to those skilled in the art which combination of time and temperature give the maximum yields. In a preferred embodiment, a solution containing about 10% by weight of a polyfunctional aromatic N-cyanoimide in an inert solvent is combined with an approximately stoichiometric amount of a diamine dissolved in an inert solvent and the mixture is warmed to $50°$ C. and allowed to stir overnight. The polyimide is recovered by pouring the reaction mixture into methanol and isolating the polymer by filtration. The yield is typically about 95–99%. The preferred inert solvents are tetrahydrofuran (THF), dimethyl sulfoxide (DMSO), N-methylpyrrolidinone (NMP), acetone, methylene chloride, ethyl acetate, dimethylformamide (DMF), and dimethylacetamide (DMAC). The molecular weight of the polyimide may be adjusted by using excess amounts of either the polyfunctional N-cyanoimide or diamine component as is apparent to those skilled in the art.

Compounds of formula I can be used as epoxy curing agents and one embodiment of the present invention is a process for curing epoxy resin with mono- or polyfunctional N-cyanoimides. One composition of the present invention is, furthermore, a hardenable mixture, and also hardened or partially hardened mixtures prepared by the process of curing said mixture, comprised of a compound of formula I wherein n is equal to or greater than 1 and a polyepoxide compound. Any polyepoxide compound can be cured by the process of the present invention and can be used to make the hardenable mixtures according to the invention. Examples of such polyepoxide compounds include but are not limited to diepoxides such as the diglycidyl ether of bisphenol-A, the tetraglycidyl ether of 1,1,2,2-tetra(4-hydroxyphenyl)ethane, 4-(2,3-epoxypropoxy)-N,N-bis(2,3-epoxypropyl)aniline, bis(4-di(2,3-epoxypropyl)aminophenyl)methane, polyglycidyl ethers of phenol-formaldehyde novolacs, the diglycidyl ether of tetrachlorobisphenol-A, the diglycidyl ether of tetrabromobisphenol-A, tetraglycidyl ethers of tetrahydroxybiphenyl, diglycidyl phthalate, diglycidyl isophthalate, diglycidyl terephthalate, the diglycidyl ether of resorcinol, triglycidyl ethers of phloroglucinol, 2,6-(2,3-epoxypropyl)phenyl glycidyl ether, the diglycidyl ether of bisphenol-F, 2,2-bis[p-(2,3-epoxypropoxy)phenyl]-1,1,1,3,3,3-hexafluoropropane, 2,2',4,4'-tetra(2,3-epoxypropoxy)benzophenone, polyglycidylethers of o-cresolformaldehyde novolacs, the diglycidyl ether of ethylene glycol, the diglycidyl ether of 1,4-butanediol, di-(2,3-epoxy-2-methylpropoxy)ethane, the triglycidyl ether of glycerol, the triglycidyl ether of trimethylolpropane, vinylcyclohexene dioxide, limonene dioxide, dicyclopentadiene dioxide, di(2,3-epoxybutyl)adipate, di(2,3-epoxybutyl) oxalate, di(2,3-epoxybutyl) azelate, di(2,3-epoxybutyl) citrate, di(2,3-epoxybutyl) phthalate, di(2,3-epoxyoctyl) tetrahydrophthalate, di(2,3-epoxyoctyl) cyclohexane-1,2-dicarboxylate, (3,4-epoxycyclohexyl)methyl 3,4-epoxycyclohexanecarboxylate, epoxidized linseed oil, epoxidized soybean oil, epoxidized methyl linoleate, epoxidized butadiene-styrene copolymers, diglydicyl ethers of hydrogenated bisphenol-A, diglycidyl ethers of hydrogenated bisphenol-F, diglycidyl esters of linoleic dimers, the triglycidyl esters of linoleic trimers, triglycidyl isocyanurate, bis(2,3-epoxycyclopentyl)ether (liquid isomer), bis(2,3-epoxycyclopentyl)ether (solid isomer).

The compounds of formula I preferred as curing agents for epoxy resins are N-cyanophthalimide, N-cyano-4-methylphthalimide, N-cyano-3,4-dimethylphthalimide, 4-bromo-N-cyanophthalimide, 4-chloro-N-cyanophthalimide, N-cyano-3,4,5,6-tetrachlorophthalimide, N-cyano-3,4,5,6-tetrabromophthalimide, N-cyano-3-fluorophthalimide, N-cyano-4-fluorophthalimide, N-cyano-3-nitrophthalimide, N-cyano-4-nitrophthalimide, N-cyanohomophthalimide, N-cyano-1,2-dihydro-3,4,5,6-tetraphenylphthalimide, N-cyanobiphenyl-2,2'-dicarboximide, N-cyano-1,8-naphthalimide, N-cyano-3-nitro-1,8-naphthalimide, 4-chloro-N-cyano-1,8-naphthalimide, N-cyanosuccinimide, N-cyano-2-hexylsuccinimide, N-cyanododecenylsuccinimide, N-cyanomaleimide, N-cyano-2-methylmaleimide, N-cyanoglutarimide, N-cyano-3,3-dimethylglutarimide, N-cyano-2,2,3,3,4,4-hexafluoroglutarimide, N-cyanocyclohexane-1,2-dicarboximide, N-cyano-4-methylcyclohexane-1,2-dicarboximide, N-cyanocyclohex-4-ene-1,2-dicarboximide, N-cyano-4-methylcyclohex-4-ene-1,2-dicarboximide, N-cyano-7-oxabicyclo[2.2.1]heptane-2,3-dicarboximide, N-cyano-7-oxabicyclo[2.2.1]hept-5-ene-2,3-dicarboximide, endo-N-cyano-5-norbornene-2,3-dicarboximide, N-cyano-1,4,5,6,7,7-hexachlorobicyclo[2.2.1]hept-5-ene-2,3-dicarboximide, endo-N-cyanobicyclo[2.2.2]oct-5-ene-2,3-dicarboximide, N,N'-dicyanocyclobutane-1,2,3,4-tetracarboximide, N,N'-dicyanocyclopentane-1,2,3,4-tetracarboximide, N,N'-dicyanocyclohexane-1,2,4,5-tetracarboximide, N,N'-dicyanotricyclo[4.2.2.0$^{2,5}$]dec-9-ene-3,4,7,8-tetracarboximide, N,N'-tetrahydrofuran-2,3,4,5-tetracarboximide, N,N'-dicyano-1,2,3,4-butane-tetracarboximide, 4,4'-bis(N-cyanocyclohexane-1,2-dicarboximide), 4,4'-methylenebis(N-cyanocyclohexane-1,2-dicarboximide), N,N'-dicyanopyromellitic diimide, N,N'-dicyanobenzophenone-3,4,3',4'-tetracarboximide, 4,4'-[(methylethylidene)bis(4,1-phenyleneoxy)]bis(1H-2-cyanoisoindole-1,3(2H)-dione), and 5,5'-[2,2,2-trifluoro-1-(trifluoromethyl)ethylidene]bis(1H-2-cyanoisoindole-1,3(2H)dione). The functional molar equivalent proportions (N-cyanoimide/oxirane ratio) of compounds of formula I which are effective in curing epoxy resins range from about 1:20 to about 1:1. The preferred amounts range from 1:10 to 1:2.

Another composition according to the invention comprises mixtures, and also hardened or partially hardened mixtures prepared by the process of curing said mixture, prepared from a compound having at least two primary amine functionalities, a compound of the formula I

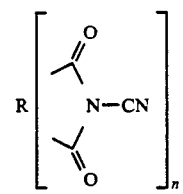

wherein R is a polyvalent aliphatic, substituted aliphatic, aromatic, or substituted aromatic radical and n is an integer having a value of 2 or greater, a reactive diluent, and any curing agent for the reactive diluent that may be necessary. The reactive diluents can be used as a carrier for the N-cyanoimide and amine monomers, and can also be used to effect the properties of the formulation.

Examples of reactive diluents are compounds containing at least one epoxide group, acrylic ester group, methacrylic ester group, lactone group, lactam group, maleimide group, nadimide group, vinyl group such as divinyl benzene or N-vinylpyrrolidinone, or allyl group such as diallyl bisphenol A.

The preferred compositions comprise mixtures and reacted mixtures of 5,5'-[2,2,2-trifluoro-1-(trifluoromethyl)ethylidene]bis(1H-2-cyanoisoindole-1,3(2H)-dione) and 4-aminophenyl sulfone with epoxy resins such as: bisphenol A diglycidyl ether, 4-(2,3-epoxypropoxy)-N,N-di(2,3-epoxypropyl)aniline, and polyglycidyl ethers of phenol-formaldehyde novolacs; mixtures of 5,5'-[2,2,2-trifluoro-1-(trifluoromethyl)ethylidene]bis(1H-2-cyanoisoindole-1,3(2H)-dione) and 2,2-bis[4-(3-aminophenoxy)phenyl] sulfone with epoxy resins such as: bisphenol A diglycidyl ether, 4-(2,3-epoxypropoxy)-N,N-di(2,3-epoxypropyl)aniline, and polyglycidyl ethers of phenol-formaldehyde novolacs; mixtures of 5,5'-[2,2,2-trifluoro-1-(trifluoromethyl)ethylidene]bis(1H-2-cyanoisoindole-1,3(2H)-dione) and 4-aminophenyl sulfone with polyfunctional methacrylic monomers such as diethylene glycol dimethacrylate, and ethoxylated bisphenol A dimethacrylate.

The hardenable mixtures above, which comprise either a mixture of a mono- or polyfunctional N-cyanoimide plus an epoxy resin or a mixture of a polyfunctional N-cyanoimide plus a diamine and an epoxy resin, can furthermore include customary modifiers such as thermoplastic polymers and elastomers and rubber toughening agents and also extenders, fillers and reinforcing agents, pigments, dyes, organic solvents, plasticizers and anti-plasticizers, leveling agents, cure accelerators, thixotropic agents, flame retarders or mould release agents.

Examples of suitable polymeric modifiers include thermoplastics such as aromatic poly(etherimides), poly(ethersulfones), and polysulfones and aliphatic polymers such as poly(vinyl acetate), poly(methyl methacrylate), and poly(vinylbutyral). Also included are rubber modifiers such as functionalized CTBN copolymers and polybutadiene polymers.

Examples of extenders, reinforcing agents, fillers and pigments which can be used in the hardenable mixtures according to the invention are: coal tar, bitumen, liquid coumarone-indene resins, textile fibers, glass fibers, asbestos fibers, boron fibers, carbon fibers, cellulose, polyethylene powder, polypropylene powder, quartz powder, mineral silicates such as mica, asbestos powder, powdered slate, kaolin, aluminum oxide trihydrate, powdered chalk, gypsum, antimony trioxide, bentonite, silicic acid aerogel, lithopone, barytes, titanium dioxide, carbon black, graphite, oxide colorants such as iron oxide, or metal powders such as aluminum powder or iron powder.

Examples of suitable organic solvents for modifying the hardenable mixtures are toluene, xylene, butyl acetate, acetone and methyl ethyl ketone.

Examples of plasticizers which can be used for modifying the hardenable mixtures are dibutyl, dioctyl and dinonyl phthalate, tricresyl phosphate, trixylenyl phosphate and diphenoxyethylformaldehyde. Examples of anti-plasticizers are the reaction product of either epoxyphenoxy propane or vinyl cyclohexene dioxide with 4-hydroxyacetanilide.

Examples of leveling agents which can be added when using the hardenable mixtures especially in the protection of surfaces are silicones, liquid acrylic resins, cellulose acetobutyrate, polyvinylbutyral, waxes, stearates and the like (some of which are also used as mould release agents).

Examples of suitable cure accelerators for modifying the cure rates and cure temperatures of the hardenable mixtures are imidazole, quaternary ammonium salts, quaternary phosphonium salts, tertiary amines, phenols, and N-(p-chlorophenyl)-N',N'-dimethylurea.

The preparation of the hardenable mixtures according to the invention can be carried out in the customary manner with the aid of known mixing equipment (stirrers, kneaders, rollers or, in the case of solid substances or powders, in mills or dry mixers). In some cases, it is necessary to warm the mixture briefly in order to achieve sufficient homogeneity.

The hardenable mixtures according to the invention are used, in particular, in the fields of the protection of surfaces, electrical engineering, lamination and fiber reinforced composite processes and adhesives technology, and in construction. They can be used, in the preparation suited in each case to the particular intended application, with or without a filler, if appropriate in the form of solutions or emulsions, as coating agents, solvent-free coatings, sinter powders, compression-molding compositions, injection-molding preparations, dipping resins, casting resins, impregnating resins, plastic foams, films, sheets, matrix materials, binders and adhesives, tooling resins, laminating resins, sealing and filling compound, floor-covering compositions and binders for mineral aggregates.

The hardening of the hardenable mixtures according to the present invention to give moldings and the like can be carried out in the temperature range of from 25° C. to about 250° C., preferably from 50° C. to about 200° C.

The compounds of formula V are poly(amide-cyanoamides)

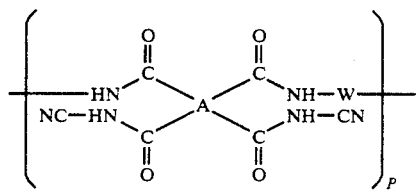

wherein A is a tetravalent aliphatic, substituted aliphatic, aromatic, or substituted aromatic radical, W is a divalent aliphatic, substituted aliphatic, aromatic, or substituted aromatic radical, and p is an integer having a value of at least 2. The polyamide-cyanoimides of formula V can be made by reacting a polyfunctional N-cyanoimide compound with a compound having at least two primary amine groups for a time and temperature sufficient to form the maximum yield of product. The compounds of formula I which are preferred in making compounds of formula V include: N,N'-dicyanocyclobutane-1,2,3,4-tetracarboximide, N,N'-dicyanocyclopentane-1,2,3,4-tetracarboximide, N,N'-dicyanocyclohexane-1,2,4,5-tetracarboximide, N,N'-dicyanotricyclo[4.2.2.0$^{2.5}$]dec-9-ene-3,4,7,8-tetracarboximide, N,N'-tetrahydrofuran-2,3,4,5-tetracarboximide, N,N'-dicyano-1,2,3,4-butane-tetracarboximide, N,N'-dicyanopyromellitic diimide, N,N'-dicyanobenzophenone-3,4,3',4'-tetracarboximide, 4,4'-[(methylethylidene)bis(4,1-phenyleneoxy)]bis(1H-2-cyanoisoindole-1,3(2H)-dione), and 5,5'-[2,2,2-trifluoro-1-(trifluoromethyl)ethylidene]bis(1H-2-cyanoisoindole-1,3(2H)-dione). Additional preferred N-cyanoimides include those of the structure shown below wherein A is an aliphatic or substituted aliphatic radical. Preferred aliphatic radicals A include the radicals originally contained in the following bis(N-cyanoimide) monomers:

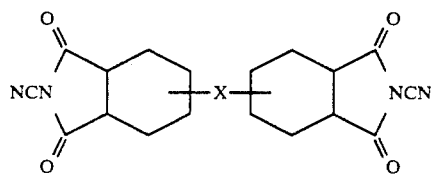

wherein X is a direct bond, O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 and R$^1$ through R$^6$ are independently hydrogen or an aliphatic or aromatic radical.

The preferred polyfunctional primary amine reactants include: 1,6-hexanediamine, triethylene glycol diamine, trimethylhexane diamine, 1,12-diaminododecane, 4,4'-diaminobicyclohexane, 1,2-, 1,3-, and 1,4-diaminobenzene, 4,4'-diaminobiphenyl, bis(4-aminophenyl)methane, 4-aminophenyl ether, 3-aminophenyl sulfone, 4-aminophenyl sulfone, 2,2-bis[(4-aminophenoxy)phenyl]propane, and 2,2-bis[4-(3-aminophenoxy)phenyl] sulfone.

The poly(amide-cyanoamides) of formula V can be used to make polyimides by heating the poly(amide-cyanoimide) to a temperature sufficient to effect ring closure and elimination of cyanamide.

One preferred method for the preparation of polyimides from poly(amide-cyanoamides) of formula V is by heating a solution of the poly(amide-cyanoamide) in a polar aprotic solvent such as DMSO or NMP to a temperature of at least 100° C. up to the boiling point of the solvent, and then isolating the resulting polyimide by any means known to those skilled in the art.

It is also preferred to carry out this reaction without solvent, simply heating the pure poly(amide-cyanoamide) to temperature ranging from 100° C. to 200° C. The poly(amide-cyanoamide) might, prior to formation of the polyimide, be mixed with reinforcing fibers, filler, or other modifiers by either melt or solvent processing techniques. It might also be fabricated into films, coatings, or adhesive bonds prior to formation of the polyimide.

The poly(amide-cyanoamides) of formula V may also be blended with reactive diluents to provide hardenable mixtures which, upon heating, form a cured material containing a polyimide. Formulations of this type utilize the ability of the poly(amide-cyanoamide) to form a polyimide without the generation of a volatile by-product such as the water which would be generated by a poly(amide-acid). The formation of polyimides from poly(amide-cyanoamides) within a formulation of this type is the most preferred method by which that process can be carried out. Such poly(amide-cyanoamide) may also be formed as intermediates during the cure of hardenable compositions comprising a polyfunctional N-cyanoimide plus a diamine and a reactive diluent such as those described above.

Another composition of this invention therefore comprises a mixture, and also hardened or partially hardened mixtures prepared by the process of curing said mixture, prepared from poly(amide-cyanoamide) of formula V plus a reactive diluent. Examples of reactive diluents are compounds containing at least one epoxide group, acrylic ester group, methacrylic ester group, lactone group, lactam group, maleimide group, nadimide group, vinyl group such as divinyl benzene or N-vinylpyrrolidinone, or allyl group such as diallyl bisphenol A. The polyfunctional epoxide compounds suitable as reactive diluents include those epoxy resins listed above as components in the N-cyanoimide/epoxy compositions of this invention.

These compositions may also include any of the modifiers described above such as polymeric modifiers and fillers and fibers and so on.

Preferred poly(amide-cyanoamides) in these compositions include the poly(amide-cyanoamides) of formula V wherein A is an aliphatic or substituted aliphatic radical. Preferred aliphatic radicals A include the radicals originally contained in the following bis(N-cyanoimide) monomers:

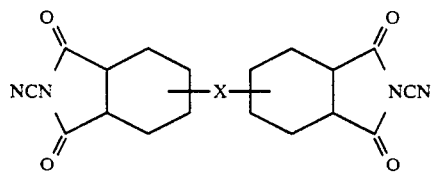

wherein X is a direct bond, O, $NR^1$, $C(CF_3)_2$, $C(CH_3)_2$, CONH, COO, $(CH_2)_m$, $CR^2R^3$, $CH(OR^4)$, $C(OR^5)(OR^6)$ and wherein m is an integer having a value of at least 1 and $R^1$ through $R^6$ are independently hydrogen or an aliphatic or aromatic radical.

Preferred poly(amide-cyanoamides) also include the poly(amide-cyanoamides) of formula V wherein W is an aromatic ring or $-(C_6H_4)-B-(C_6H_4)-$ wherein B is $CH_2$, O, CO, OCO—R—COO wherein R is an aliphatic or aromatic radical, $SO_2$, $C(CH_3)_2$, $C(CF_3)_2$, $C(CH_3)_2-(C_6H_4)-C(CH_3)_2$, $O-(C_6H_4)-O$, $O-(C_6H_4)-C(CH_3)_2-(C_6H_4)-O$, or $O-(C_6H_4)-SO_2-(C_6H_4)-O$. Other preferred structures for W include $-(CHR^1-CHR^2-O)_m-$ and $-(CR^1R^2)_m-$ wherein m is an integer having a value of one or greater and $R^1$ and $R^2$ are independently hydrogen or an aliphatic radical.

The compositions may contain from 1 to 95 weight percent of the poly(amide-cyanoamide). At the lower weight percents, the poly(amide-cyanoamide) serves as a polymeric modifier for the thermosetting reactive diluent. At the higher weight percents, the reactive diluent serves as a carrier and processing modifier for the poly(amide-cyanoamide).

Like the other hardenable compositions of this invention, the above compositions may be prepared by standard blending techniques familiar to those skilled in the art. They may also be used in a wide range of applications such as those already listed.

The hardening or curing of these compositions can be carried out in a temperature range of about 25° C. to 350° C., preferably from 50° C. to 200° C.

The compounds of the formula II are dianhydrides

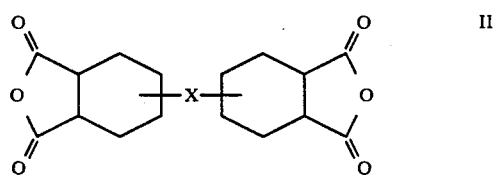

wherein X is a direct bond, O, $NR^1$, $C(CF_3)_2$, $C(CH_3)_2$, CONH, COO, $(CH_2)_m$, $CR^2R^3$, $CH(OR^4)$, $C(OR^5)(OR^6)$ and wherein m is an integer having a value of at least 1 and $R^1$ through $R^6$ are independently hydrogen or an aliphatic or aromatic radical. An aliphatic radical is any mono-valent saturated, unsaturated, linear, or cyclic aliphatic moiety. These aliphatic moieties include those moieties which contain heteroatoms, examples of which include alkoxy, and amino groups. An aromatic radical is a substituted or unsubstituted mono-valent carbocyclic or heterocyclic aromatic ring. The preferred compounds of formula II are those in which X is O, $CH_2$, CHOH, CH(OMe), and 1,1,1,3,3,3-hexafluoropropyl. These dianhydrides are useful precursors for both N-cyanoimide monomers and for polyimide products.

The compounds of formula II can be made by the process which comprises, as a first step, hydrogenating a compound of the formula III

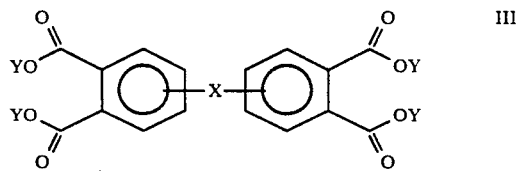

wherein X is defined as above and Y is an aliphatic or aromatic radical in the presence of a catalyst effective amount of a noble metal catalyst to form a reduced reaction product. An aliphatic radical is any mono-valent saturated, unsaturated, linear, or cyclic moiety. An aromatic radical is a substituted or unsubstituted mono-valent carbocyclic or heterocyclic aromatic ring. The noble metal catalyst can be any noble metal catalyst normally used in hydrogenation reactions of aromatic compounds and which are well known in the art such as platinum, palladium, rhodium, and ruthenium as well as nickel alloys such as Raney nickel. Preferred catalysts are platinum oxide, Raney nickel, rhodium on alumina, rhodium on carbon, ruthenium on alumina, and ruthenium on carbon. Preferably, the hydrogenation is carried out in a polar solvent such as a methanol/acetic mixture, or tetrahydrofuran, or tetrahydrofuran/acetic acid mixtures at about 110° C. to about 130° C. at a hydrogen pressure of about 2000 psi. The reduced reaction product has the general formula

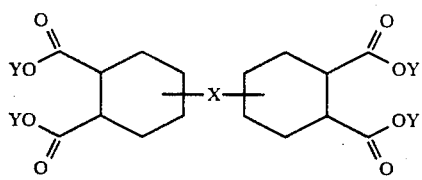

wherein X and Y are defined as above. Preferably, Y is a simple alkyl radical such as methyl or ethyl. The reduced reaction product is then hydrolyzed to the tetracarboxylic acid by any standard ester hydrolysis method well known to those skilled in the art. The preferred hydrolysis method is treating the reduced ester with an aqueous caustic solution in the presence of a suitable cosolvent such as methanol, followed by acidification, and isolation of the product by any method known to those skilled in the are such as by filtration. The tetracarboxylic acid obtained from the hydrolysis reaction can then be converted to the dianhydride by any method well known to those skilled in the art such as by heating the acid or refluxing it in the presence of a carboxylic acid anhydride. The preferred method is by refluxing the tetracarboxylic acid with acetic anhydride.

A modification of this process is particularly preferred whereby compounds of formula II can be prepared directly from dianhydrides of the general formula VII

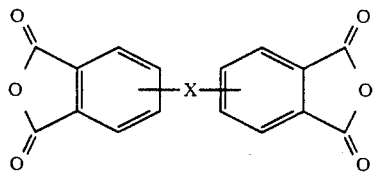

wherein X is defined as above. This process comprises the steps of: (1) hydrogenation of a compound of the formula VII wherein X is defined as above in the presence of a noble metal catalyst in an alcoholic solvent as described above and in the presence of a catalyst effective amount of an esterification catalyst; (2) hydrolysis of the reduced product to the tetracarboxylic acid; (3) conversion of the tetracarboxylic acid to the dianhydride by any method known to those skilled in the art. Preferred solvents include methanol, ethanol, propanol, n-butanol, isopropanol, or mixtures thereof. Preferred esterification catalysts include mineral acids such as sulfuric acid, hydrochloric acid, or phosphoric acid, or organic acids such as trifluoroacetic acid.

The compounds of formula IV are polyimides

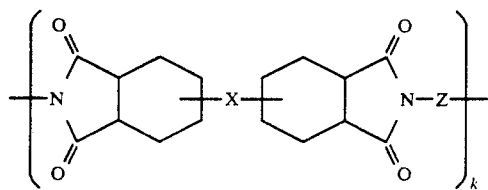

wherein X is defined as above and Z is one or more substituted or unsubstituted divalent carbocyclic or heterocyclic rings, a divalent moiety containing two benzylic sites such as p-xylenediylidene or p-bitoluenediylidene, or a divalent aliphatic radical wherein the atom γ to the imide nitrogen is a saturated carbon atom or a nitrogen, oxygen or divalent sulfur atom. The atom γ to the imide nitrogen, atom G in formula VIII, is three positions removed from the imide nitrogen atom.

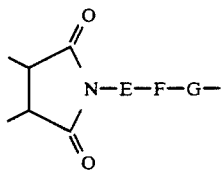

The polyimides of formula IV can be made by the process disclosed above for making polyimides by reacting polyfunctional aliphatic N-cyanoimides of formula I and a compound having at least two primary amine functionalities. The polyimides of formula IV may also be prepared directly from the appropriate dianhydride and diamine by standard procedures well known to those skilled in the art.

Compounds of the formula VI

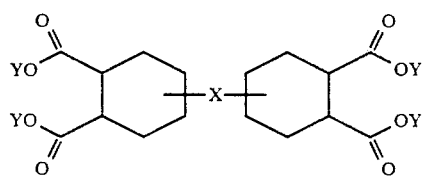

are tetraesters wherein X is O, NR$^1$, C(CF$_3$)$_2$, C(CH$_3$)$_2$, CONH, COO, (CH$_2$)$_m$, CR$^2$R$^3$, CH(OR$^4$), C(OR$^5$)(OR$^6$) and wherein m is an integer having a value of at least 1 R$^1$ through R$^6$ are independently hydrogen or an aliphatic or aromatic radical and Y is an aliphatic or aromatic radical. An aliphatic radical is any monovalent saturated, unsaturated, linear, or cyclic moiety. An aromatic radical is a substituted or unsubstituted mono-valent carbocyclic or heterocyclic aromatic ring. Compounds of the formula VI can be made by hydrogenating the corresponding tetraester in the presence of a catalyst effective amount of a noble metal catalyst. The noble metal catalyst can be any noble metal catalyst normally used in hydrogenation reactions of aromatic compounds and which are well known in the art such as platinum, palladium, rhodium, and ruthenium as well as nickel alloys such as Raney nickel. Preferred catalysts are platinum oxide, Raney nickel, rhodium on alumina, rhodium or carbon, ruthenium on alumina, and ruthenium on carbon. The hydrogenation may be carried out neat or in a polar solvent such as a methanol/acetic mixture, or tetrahydrofuran, or tetrahydrofuran/acetic acid mixtures at about 110° C. to about 130° C. at a hydrogen pressure of about 2000 psi.

The following examples are meant to illustrate but not limit the invention.

EXAMPLE 1

Preparation of
1,3-Dihydro-1,3-dioxo-2H-isoindole-2-carbonitrile
(N-Cyanophthalimide)

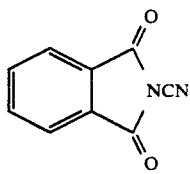

To a 25 mL round-bottomed flask was added phthalimide (1.47 g, 10.0 mmol), cyanogen bromide (1.27 g, 12.0 mmol), and 10 mL of reagent grade acetone. The resulting mixture was cooled using an ice/salt bath while triethylamine (1.8 mL, 12.8 mmol) was added dropwise over a 2 minute period. After 15 minutes, the mixture was transferred to a separatory funnel and partitioned between ethyl acetate and water. The organic phase was washed with water, saturated brine, dried (MgSO$_4$), and filtered. The solution was decolorized with activated charcoal, and concentrated to give a brown solid. This material was recrystallized from ethyl acetate to give 1.32 g (77%) of a brown crystalline solid, mp 189°–191° C. (reported in Zh. Org. Khim. 1977, 13, 968 as 190° C.): IR (nujol) 2258 (nitrile), 1755 (carbonyl) cm$^{-1}$; $^1$H NMR (200 MHz, DMSO) δ 8.05–8.15 (m, 4); $^{13}$C NMR (50 MHz, DMSO) δ 162.61, 136.35, 130.76, 125.03, 102.86.

COMPARATIVE EXAMPLE 1

Preparation of
1,3-Dihydro-1,3-dioxo-2H-isoindole-2-carbonitrile(N-Cyanophthalimide)

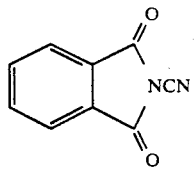

To a 1 L 3-necked flask equipped with an overhead mechanical stirrer, thermocouple, and a pressure equalizing addition funnel was added phthaloyl dichloride (100.7 g, 0.496 mol), and 350 mL of THF. A mixture of cyanamide (22.0 g, 0.523 mol) and 0.5 g of DMAP was dissolved in 75 mL of THF and 140 mL (1.00 mol) of triethylamine, and the resulting solution was transferred to the addition funnel. Under a nitrogen atmosphere, the cyanamide solution was added dropwise at such a rate that with external cooling the reaction temperature was kept below 5° C., about 3 h. The resulting slurry was allowed to stir at 0° C. for 0.5 h, then allowed to warm to room temperature over a 2 h period. The slurry was transferred to a separatory funnel and partitioned between ethyl acetate and dilute hydrochloric acid. The organic phase was washed with brine, dried (MgSO$_4$), and concentrated using a rotary evaporator. The yellow crystalline product was recrystallized from a mixture of THF/hexanes to afford 66.4 g (82%), combined yield from several crops, of light yellow crystals, mp 189°–190° C. This material was spectroscopically identical to the material obtained in example 1.

EXAMPLE 2

Preparation of
1,3-Dihydro-5-nitro-1,3-dioxo-2H-isoindole-2-carbonitrile

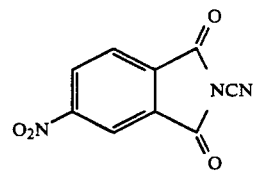

A 25 mL round-bottomed flask was charged with 4-nitrophthalimide (0.96 g, 5.0 mmol), cyanogen bromide (0.64 g, 6.0 mmol), and 10 mL of reagent grade acetone. The resulting suspension was cooled using an ice/salt bath, and triethylamine (1.0 mL, 7.1 mmol) was added dropwise over a 4 minute period. The mixture was allowed to stir for 20 minutes before being partitioned between ethyl acetate and water. The organic phase was washed with water, saturated brine, dried (MgSO$_4$), and concentrated to give 0.95 g of a yellow solid. This material was recrystallized from ethyl acetate to afford 0.65 g (60%) of yellow crystals, mp 209.5°–210.5° C. (reported in Zh. Org. Khim. 1977, 13, 968 as 215° C.): IR (nujol) 2261 (nitrile), 1811 (carbonyl), 1769 (carbonyl), 1533 (nitro), 1343 (nitro) cm$^{-1}$; $^1$H NMR (200 MHz, DMSO) δ 8.34 (d, 1, J=8.9 Hz), 8.70–8.78 (m, 2); $^{13}$C NMR (50 MHz, DMSO) δ 161.15, 160.92, 152.34, 135.19, 132.10, 131.16, 126.48, 119.76, 102.26; GC/MS (relative intensity) 217 (77.8), 149 (71.7), 103 (64.4), 75 (100), 74 (52.7).

EXAMPLE 3

Preparation of
N-Cyano-cis-4-cyclohexene-1,2-dicarboximide

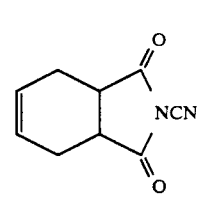

Using a 250 mL round-bottomed flask equipped with a magnetic stir bar and an ice/salt bath, a suspension of cis-4-cyclohexene-1,2-dicarboximide (15.1 g, 100 mmol), cyanogen bromide (11.7 g, 110 mmol), and 100 mL of acetone was cooled to 0° C. Triethylamine (16.0 mL, 115 mmol) was added via syringe over a 12 minute period. The resulting peach slurry was allowed to stir for 15 minutes. The mixture was diluted with ethyl acetate and filtered to remove solid triethylamine hydrobromide. The filter cake was rinsed with ethyl acetate and the filtrate was concentrated using a rotary evaporator. The crude paste was partitioned between water and a 2:1 mixture of ethyl acetate/hexanes. The organic phase was washed with brine, dried (MgSO$_4$), and concentrated to give a light brown solid. The crude product was purified by recrystallization using ethyl acetate/pet ether or ethyl acetate/hexanes to afford 11.5 g (65%) of a glossy off white solid, mp 136°–138° C.: IR (nujol) 2256 (nitrile), 1749 (carbonyl) cm$^{-1}$; $^1$H NMR (200 MHz, CDCl$_3$) δ 2.30 (ddd, 2, J=15, 4.4, 2.75 Hz), 2.64 (ddd, 2, J=15, 3.8, 2.75 Hz), 3.35 (dd, 2, J=3.5, 2.75 Hz), 5.98 (ddd, 2, J=3.9, 1.7, 1.5 Hz); $^{13}$C NMR (50 MHz, CDCl$_3$) δ 173.48, 127.52, 100.72, 40.08, 23.26; GC/MS m/e (relative intensity) 176 (29.5), 147 (11.1), 107 (20.0), 105 (23.3), 80 (44.0), 79 (100), 78 (35.1).

EXAMPLE 4

Preparation of 1,3-Dihydro-1,3-dioxo-5-methyl-2H-isoindole-2-carbonitrile

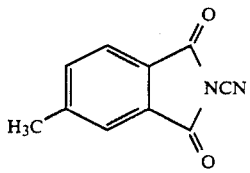

To a 250 mL round-bottomed flask was added 4-methylphthalimide (10.00 g, 62.0 mmol), prepared as described below, cyanogen bromide (7.00 g, 66.00 mmol), magnetic stir bar, and 75 mL of reagent grade acetone. The resulting slurry was cooled using an ice/salt bath. With cooling and vigorous stirring, triethylamine (10.0 mL, 71.7 mmol) was added via syringe over a 15 minute period. The resulting red slurry was allowed to stir for 10 minutes, the cooling bath was removed, and the mixture was allowed to warm to room temperature, about 10 minutes. The solution was filtered to remove the precipitated triethylamine hydrobromide. The solids were washed with ethyl acetate, and the combined filtrates were concentrated using a rotary evaporator. The crude product was transferred to a separatory funnel and partitioned between 2N hydrochloric acid and a 2:1 mixture of ethyl acetate/hexanes. The organic phase was washed with brine, and dried (MgSO$_4$). The solution was filtered through a short bed of silica gel, then concentrated using a rotary evaporator to give a yellow solid. This material was purified by recrystallization from a mixture of ethyl acetate and toluene to yield 8.22 g (71%) of brownish yellow crystals, mp 155°–158° C.: IR (KBr) 2256 (nitrile), 1792, 1761, 1742, 1610 cm$^{-1}$; $^1$H NMR (200 MHz, DMSO) δ 2.51 (s, 3), 7.75–8.00 (m, 3); $^{13}$C NMR (50 MHz, DMSO) δ 162.60, 162.38, 147.99, 136.83, 130.99, 127.99, 125.31, 124.94, 102.84, 43.22; GC/MS m/e (relative intensity) 186 (82.9), 142 (9.1), 119 (8.9), 118 (100), 90 (38.3), 89 (45.2), 63 (33.5), 62 (13.6).

The imide was prepared as follows. To a 500 mL round-bottomed flask equipped with a magnetic stir bar was added 100 mL of concentrated ammonium hydroxide solution. The ammonium hydroxide solution was cooled using an ice/salt bath while 4-methylphthalic anhydride (27.75 g, 171.1 mmol) was added over a 30 minute period. The resulting thick white slurry was allowed to stir at room temperature for 1 h, then at 50° C. for 2.5 h. The solvent was removed by distillation, and the residue was heated to 220° C. for 2 h. After cooling, the fine white needles that had collected at the top of the flask were pushed down, and the mixture heated an additional 1.5 h at 230° C. The molten mixture was allowed to cool and afforded 23.7 g of a hard yellow solid. The solid mass was pulverized and dissolved in a refluxing mixture of acetone/methanol (300 mL of acetone, 50 mL of methanol), and the solution was allowed to cool. The crystalline product was isolated by filtration and dried under vacuum. This afforded 16.25 (59%) of fine yellow crystals, mp 196°–198° C. (reported mp is 195°–196° C., J. Org. Chem. 1977, 42, 3442). The filtrate was partially concentrated and allowed to cool, yielding an additional 7.20 g (26%) of yellow crystals, total yield was 23.45 g (85%). Both samples were found to be >99% pure by GC analysis: IR (KBr) 3210 (N-H), 1769 (carbonyl), 1732 (carbonyl), 1359, 1302, 1047, 741 cm$^{-1}$; $^1$H NMR (200 MHz, DMSO) δ 2.40 (s, 3), 7.45–7.65 (m, 3), 10.9 (s, broad, 1); $^{13}$C NMR (50 MHz, DMSO) δ 169.17, 169.09, 144.99, 134.50, 132.90, 129.94, 123.14, 122.64, 21.28; GC/MS m/e (relative intensity) 161 (100), 118 (54.0), 117 (26.8), 90 (33.2), 89 (26.3), 63 (10.3).

EXAMPLE 5

Preparation of 4,4'-[(1-Methylethylidene)bis(4,1-phenyleneoxy)]-bis(1H-isoindole-1,3(2H)-dione)

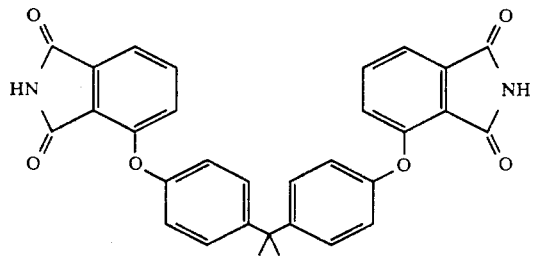

To a 500 mL round-bottomed flask equipped with an ice/salt cooling bath was added 25 mL of concentrated ammonium hydroxide solution. Over a period of 1 h, 10.00 g (19.21 mmol) of 4,4'-[(methylethylidene)bis(4,1-phenyleneoxy)]bis(1,3-isobenzofurandione) was added to the stirred solution. The cooling bath was removed, and the mixture was allowed to stir for 30 minutes. The excess ammonium hydroxide solution was removed by distillation (caution: vigorous foaming), and the dark residue was heated to 220° C. under vacuum (<2 torr) for 2 h. After cooling the dark solid was chipped out of the flask. The crude product was purified by recrystallization from toluene/methanol to give a total of 8.81 g (88%) combined from three crops of crystals, mp 258°–260° C. IR (nujol) 3190 (N-H), 1771, 1725 (carbonyl), 1504, 1266 (C-O) cm$^{-1}$; $^1$H NMR (200 MHz, DMSO) δ 1.67 (s, 6), 7.04 (d, 4, J=8.8 Hz), 7.13 (dd, 2, J=0.7, 8.3 Hz), 7.30 (d, 4, J=8.8 Hz), 7.53 (dd, 2, J=0.7, 7.3 Hz), 7.74 (dd, 2, J=7.3, 8.3 Hz), 11.3 (broad, 2); $^{13}$C NMR (50 MHz, DMSO) δ 168.46, 166.95, 153.37, 153.04, 146.34, 136.51, 135.03, 128.25, 123.56, 120.19, 118.77, 117.50, 41.85, 30.53; mass spectrum m/e (relative intensity) 518 (11.2), 504 (25.6), 503 (100.0), 264 (22.2), 246 (28.3), 179 (38.4), 146 (35.8), 75 (77.3).

EXAMPLE 6

Preparation of
4,4'-[(1-Methylethylidene)bis(4,1-phenyleneoxy)]-
bis(1H-2-cyanoisoindole-1,3(2H)-dione)

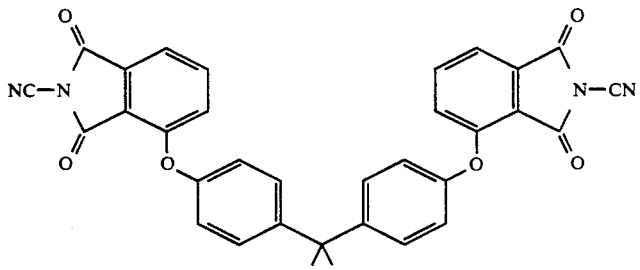

To a 100 mL round-bottomed flask was added 4,4'-[(methylethylidene)bis(4,1-phenyleneoxy)]bis(1H-isoindole-1,3(2H)-dione) (3.00 g, 5.8 mmol), from example 5, cyanogen bromide (1.42 g, 14.2 mmol), and 30 mL of reagent grade acetone. The resulting slurry was cooled using an ice/salt bath while triethylamine (2.2 mL, 15.8 mmol) was added via syringe over a 2 minute period. The mixture was allowed to stir an additional 15 minutes, then poured into a mixture of ethyl acetate/hexanes (9 to 1, about 100 mL). The solution was filtered and concentrated using a rotary evaporator to give a dark residue. The crude product was filtered through a bed of silica gel using a 7:3 THF/hexanes solution as solvent. Concentration of this solution by rotary evaporation gave a viscous oil which later gave 2.85 g of a brown amorphous solid as residual solvent was removed under vacuum. Proton NMR analysis showed residual traces of ethyl acetate, THF, and diethylcyanamide. The yield was 86% of material in a purity exceeding 90%. Typical spectrographic analysis provided the following information. IR (KBr) 2261 (nitrile), 1773, 1752 (carbonyl), 1504, 1274 (C-O), 816 (aromatic) cm$^{-1}$; $^{13}$C NMR (50 MHz, DMSO) δ 102.70 (nitrile).

EXAMPLE 7

Preparation of
5,5'-[2,2,2-Trifluoro-1-(trifluoromethyl)ethylidene]-
bis(1H-isoindole-1,3(2H)-dione)

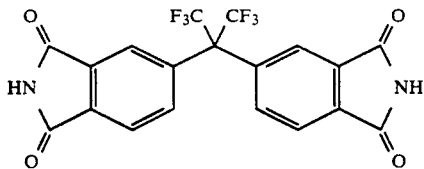

A 500 mL round-bottomed flask was charged with 100 mL of concentrated ammonium hydroxide solution and cooled using a cracked ice/salt bath. Over a period of 1 h, 50.00 g (112.5 mmol) of 5,5'-[2,2,2-trifluoro-1-(trifluoromethyl)ethylidene]bis(1,3-isobenzofurandione) was added. An additional 50 mL of ammonium hydroxide solution and 50 mL of THF were added to help keep the slurry suspended. The resulting slurry was allowed to stand overnight at room temperature. The suspended solids readily dissolved as the mixture was warned. The THF and ammonium hydroxide were removed by distillation, and the residue was heated to 220° C. for 4 h under vacuum (<2 torr). The resulting solid was allowed to cool. This gave 49.0 g (98%) of an off white solid, mp 322° C. (DSC): IR (nujol) 3300 (N-H), 1717 (carbonyl), 1196, 1260 (C-F) cm$^{-1}$; $^1$H NMR (200 MHz, DMSO) δ 7.63 (broad, 2), 7.81 (d, 2, J=8.1 Hz), 7.99 (d, 2, J=8.1 Hz), 11.62 (s, 2); $^{13}$C NMR (50 MHz, DMSO) δ 168.35, 168.24, 137.22, 133.98, 133.55, 123.91, 123.4 (q, 2, J$_{CF}$=285.5 Hz), 123.54, 64.5 (m, 1); GC/MS m/e (relative intensity) 442 (100), 441 (72), 423 (26), 399 (23), 398 (52), 355 (66), 178 (75), 75 (52).

EXAMPLE 8

Preparation of
5,5'-[2,2,2-Trifluoro-1-(trifluoromethyl)ethylidene]-
bis(1H-2-cyanoisoindole-1,3(2H)-dione)

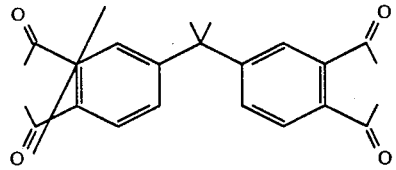

A suspension of 5,5'-[2,2,2-trifluoro-1-(trifluoromethyl)ethylidene]bis(1H-isoindole-1,3(2H)-dione) (30.00 g, 67.83 mmol), example 7, and cyanogen bromide (15.0 g, 141.6 mmol) in 200 mL of reagent grade acetone was cooled to approximately 0° C. using an ice/salt bath. Triethylamine (21.0 mL, 150 mmol) was added via syringe over a 15 minute period. The resulting mixture was allowed to stir at 0° C. for 30 minutes, the bath was removed, and stirring was continued for 30 minutes. The reaction mixture was diluted with ethyl acetate, filtered, and concentrated using a rotary evaporator. The residue was transferred to a separatory funnel, and partitioned between ethyl acetate and dilute hydrochloric acid. The organic phase was washed with saturated brine, dried (MgSO$_4$), and concentrated to give a pasty solid. This material was dissolved in 150 mL of refluxing THF. Hexanes were added to the refluxing solution until clouding. As the solution cooled small light yellow granular crystals formed. Over several hours, 400 mL of additional hexanes were added. The product was isolated by filtration, and dried under vacuum to afford 28.85 g (86%) of a light yellow solid: IR (nujol) 2259 (nitrile), 1769 (carbonyl), 1218, 1260 (C-F), 717 (aromatic) cm$^{-1}$; $^{13}$C NMR (50 MHz, DMSO) δ 161.69, 161.52, 138.64, 137.28, 132.26, 131.91, 126.09, 125.12, 123 (CF$_3$, q, J$_{CF}$≈290 Hz), 102.32.

Examples 9, 10, and 11 demonstrate the preparation of N-substituted imides from N-cyanoimides.

EXAMPLE 9

A 50 mL round-bottomed flask was charged with N-cyanophthalimide (1.72 g, 10.0 mmol), 0.13 g octadecane (GC internal standard), and 20 mL of THF. To this mixture was added a solution of 4-aminophenyl ether (1.00 g, 5.0 mmol) in 3 mL of NMP. Within 30 minutes, all of the 4-aminophenyl ether had been consumed, as determined by GC. The solution was warmed to 50° C. and allowed to stir overnight. The resulting grey precipitate was isolated by filtration, dried under reduced pressure to afford 1.61 g (70%) of a fine grey powder, mp 285.0°–286.5° C. Analysis of the spectroscopic properties of this material was consistent with the diimide structure shown below.

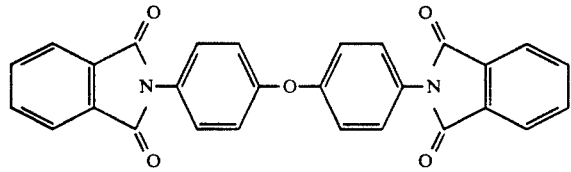

EXAMPLE 10

To a solution of N-cyanophthalimide (1.42 g, 8.25 mmol) in 20 mL of THF was added 0.10 g octadecane (GC internal standard), and a solution of 3-aminophenyl sulfone (1.00 g, 4.03 mmol) in 3 mL of NMP. The resulting mixture was warmed to 50° C. and allowed to stir for 24 h. The resulting slurry was filtered, and the isolated solid was rinsed with ether. The solid was dried under reduced pressure to yield 1.35 g (66%) of a pale peach colored solid, mp. 313°–314° C. (reported in Int. J. Adhes, Adhes. 1985, 5, 183 as 317°–320° C.). Analysis of the spectroscopic properties of this material was consistent with the diimide structure shown below.

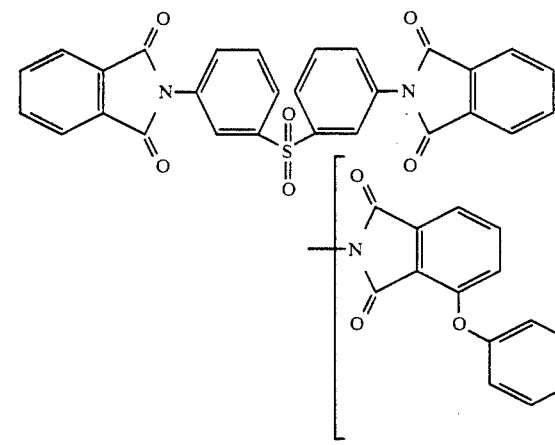

EXAMPLE 11

To a 50 mL round-bottom flask was added N-cyanophthalimide (1.42 g, 8.25 mmol), 0.05 g octadecane (GC internal standard), and 20 mL of THF. To this was added a solution of 4-aminophenyl sulfone (1.00 g, 4.03 mmol) in 3 mL of NMP. The solution was warmed to 50° C. and allowed to stir for 2 days. The resulting slurry was filtered, and the isolated solid was rinsed with THF. The solid was dried under reduced pressure to afford 0.71 g (35%) of a white powder, mp 310°–314° C. Analysis of the spectroscopic properties of this material was consistent with the diimide structure shown below.

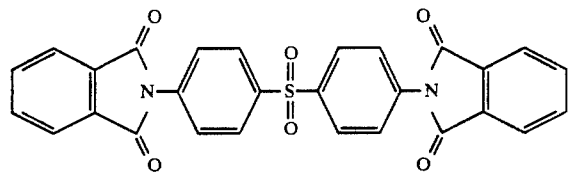

Examples 12 through 16 demonstrate the preparation of polyimides from bis-N-cyanoimides and diamines in an inert solvent.

EXAMPLE 12

To a solution of 4,4'-[(1-methylethylidene)bis(4,1-phenyleneoxy)]bis(1H-2-cyanoisoindole-1,3(2H)-dione), 1.00 g, in 25 mL of THF was added a solution of 4-aminophenyl ether, 0.35 g, in a 1:1 mixture of THF/NMP, $\approx$2 mL. The resulting solution was warmed to 50° C. and allowed to stir for 5 h. During the course of the reaction an oily residue formed at the bottom of the flask. The THF solution was decanted, the residue was dissolved in $\approx$15 mL of DMSO, and precipitated by slow addition to 150 mL of rapidly stirred water. The precipitate was isolated by filtration, and rinsed several times with methanol. This material was dried overnight in a vacuum oven and afforded 0.85 g (70%) of a grey powdery solid. A glass transition temperature of 228° C. (DSC) was observed (reported as 235° C. in Polym. Prepr. (Am. Chem. Soc., Div. Polym. Chem.) 1983, 24, 312). Analysis of the spectroscopic properties of this material was consistent with the polyimide structure shown below.

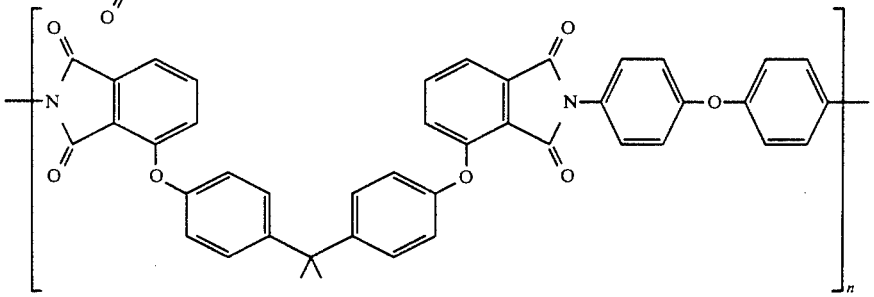

EXAMPLE 13

A 25 mL round-bottomed flask was charged with 1.00 g of 4,4'-[(methylethylidene)bis(4,1-phenyleneoxy)]bis(1H-2-cyanoisoindole-1,3(2H)-dione), 0.70 g of 2,2-bis[(4-aminophenoxy)phenyl]propane (BAPP), and 10 mL of DMSO. The resulting solution was warmed to 50° C. and allowed to stir for 5 h. The polymer was precipitated in methanol, and isolated by filtration. The resulting solid was dried in a vacuum oven to afford 1.56 g of a tan powder. Analysis of the spectroscopic properties of this material was consistent with the polyimide structure shown below.

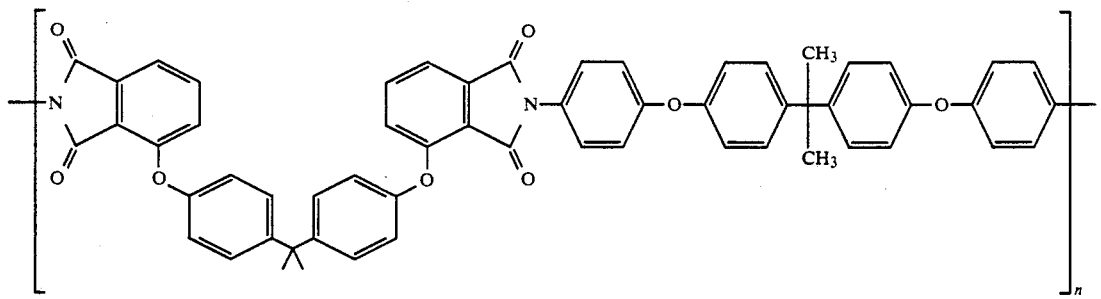

A solution of this material, ≈10% in THF, was evaporated onto a piece of glass matting. The sample was analyzed by DMA and a glass transition temperature of 215° C. was observed.

EXAMPLE 14

A 50 mL round-bottomed flask was charged with 5,5'-[2,2,2-trifluoro-1-(trifluoromethyl)ethylidene]-bis(1H-2-cyanoisoindole-1,3(2H)-dione) (2.00 g, 4.06 mmol), 4-aminophenyl ether (0.82 g, 4.06 mmol), and 20 mL of DMSO. The resulting mixture was warmed to 50° C. and allowed to stir for 5 h. The polymer was precipitated into 400 mL of rapidly stirring methanol. The precipitate was isolated by filtration, rinsed several times with methanol, and dried in a vacuum oven to yield 2.46 g (99%) of a grey powdery solid. Analysis of the spectroscopic properties of this material was consistent with the polyimide structure shown below.

2,2-bis[(4-aminophenoxy)phenyl]propane (BAPP). The resulting solution was warmed to 50° C. and allowed to stir for 5 h. The polymer was precipitated into 100 mL of rapidly stirring methanol, isolated by filtration, and dried in a vacuum oven to afford 1.15 g (90%) of a light yellow powder. Analysis of the spectroscopic properties of this material was consistent with the polyimide structure shown below.

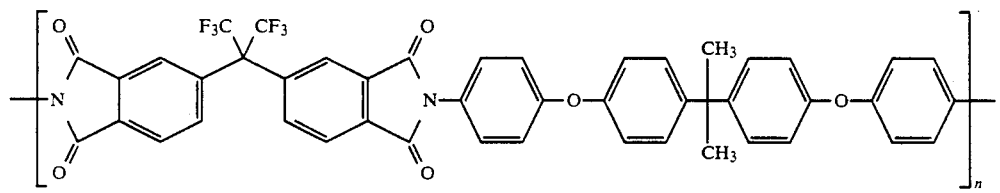

A solution of this material, ≈30% in THF, was evaporated onto a piece of glass matting. The sample was analyzed by DMA and a glass transition temperature of 250° C. was observed.

EXAMPLE 16

To a solution of 5,5'[2,2,2-trifluoro-1-(trifluoromethyl)ethylidene]bis(1H-2-cyanoisoindole-1,3(2H)-dione), 1.00 g, in 10 mL of DMSO was added 0.65 g of EPON HPT ™ curing agent 1061-M (aromatic di-

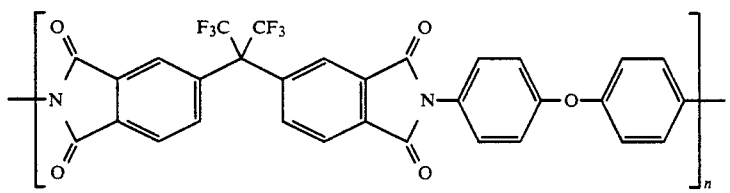

A solution of this material, ≈25% in THF, was evaporated onto a piece of glass matting. The sample was analyzed by DMA and a glass transistion temperature of 287° C. was observed.

EXAMPLE 5

To a solution of 5,5'-[2,2,2-trifluoro-1-(trifluoromethyl)ethylidene]bis(1-H-2-cyanoisoindole-1,32H)-dione), 0.77 g, in 8 mL of DMSO was added 0.62 g of amine available from Shell Chemical Company). The resulting solution was warmed to 50° C. and allowed to stir for 5 h. The polymer was precipitated into methanol and isolated by filtration. The polymer was rinsed with methanol, then dried in a vacuum oven to afford 1.21 g (85%) of a light yellow solid. Analysis of the spectroscopic properties of this material was consistent with the polyimide structure shown below.

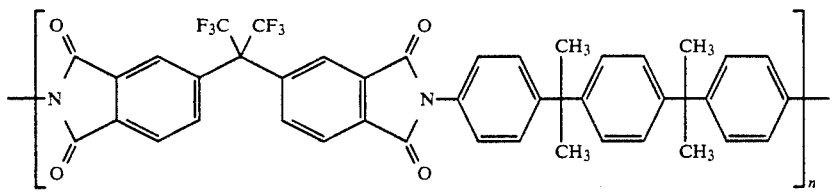

A solution of this material, ≈30% in THF, was evaporated onto a piece of glass matting. The sample was analyzed by DMA and a glass transition temperature of 260° C. was observed (reported as 267° C. in Polym. Prepr. (Am. Chem. Soc., Div. Polym. Chem.) 1988, 29, 349).

Examples 17 through 24 demonstrate the preparation and curing of compositions comprising a bis-N-cyanoimide, a diamine, and an epoxy diluent.

EXAMPLE 17

To a 100 mL 3-necked pyrex resin flask equipped with an overhead stir motor and gas inlet was added 6.00 g of ground and sieved 5,5'-[2,2,2-trifluoro-1-(trifluoromethyl)ethylidene]bis(1H-2-cyanoisoindole-1,3(2H)-dione) (6F-DCI), 2.05 g of Tactix H41 (liquid aromatic diamine from Dow Chemical Company), and 8.05 g of MY 0510 (trifunctional epoxy resin from Ciba-Geigy). The mixture was allowed to stir until the components were evenly blended. The stirring rate was reduced, but not stopped, and a vacuum was applied to the system. The resin mixture was allowed to degas for a short period of time. At this point the stirring was stopped, and the reactor brought back to atmospheric pressure.

Samples of resin used for adhesive and thermal analysis were cured using an oven temperature of 180° C., and a 1 h cure schedule.

Adhesive performance was determined by a tensile lap shear test based upon the US ASTM D1002-72 standard. Test coupons were made of aluminum alloy ALC2024-T3 whose dimensions were 4×1×0.63 inches. The adhesive specimens were prepared by sanding and degreasing about a 1″ length on each of two coupons. Adhesive was spread onto the abraded surfaces which were then clamped together to form ½ inch of overlap. The test specimens were held together during cure using a pair of #50 binding clips. Lap shear strengths were determined for the adhered coupons using an Instron tensile tester with a crosshead speed of 0.050 inches/min. Lap shear strengths were measured at room temperature as well as at elevated temperatures. The results are given in table 1.

Thermal properties, specifically glass transition temperatures ($T_g$), were, unless otherwise noted, determined by DMA methods using a DuPont Instruments Dynamic Mechanical Analyzer with a scanning rate of 5° or 10° C./min. Test specimens were cured in aluminum pans and cut to size suitable for analysis. The reported $T_g$ values represents the maximal value obtained for the loss modulus curve (E″). For samples which gave poorly defined loss modulus curves, midpoint values of the storage modulus curves (E′) were used instead. The results are given in table 1.

EXAMPLE 18

In the manner described in example 7, an adhesive composition containing 6.00 g of 6F-DCI, 5.27 g of 2,2-bis[4-(3-aminophenoxy)phenyl] sulfone (SED-M), and 11.27 g of EPON 828 (difunctional epoxy resin from Shell Chemical Company) was prepared and tested. The results are given in table 1.

EXAMPLE 19

In the manner described in example 17, an adhesive composition containing 4.51 g of 6F-DCI, 1.51 g of 4-aminophenyl sulfone (4-DDS), and 4.01 g of MY 0510 was prepared and tested. The results are given in table 1.

EXAMPLE 20

In the manner described in example 17, an adhesive composition 6.00 g of 6F-DCI, 3.03 g of 4-DDS, and 9.03 g of MY 0510 was prepared and tested. The results are given in table 1.

EXAMPLE 21

In the manner described in example 17, an adhesive composition containing 6.00 g of 6F-DCI, 3.03 g of 4-DDS, 13.54 g of MY 0510, and 8.00 g of aluminum oxide was prepared and tested. The results are given in table 1.

EXAMPLE 22

In the manner described in example 17, an adhesive composition containing 6.00 g of 6F-DCI, 3.03 g of 4-DDS, 3.4 g of MY 0510, and 3.4 g of EPON 828 was prepared and tested. The results are given in table 1.

EXAMPLE 23

In the manner described in example 17, an adhesive composition containing 7.62 g of 6F-DCI, 3.85 g of 4-DDS, and 8.60 g of Araldite CY 179 (cycloaliphatic epoxy resin from Ciba-Geigy) was prepared and tested. The results are given in table 1.

EXAMPLE 24

In the manner described in example 17, an adhesive composition containing 6.00 g of 6F-DCI, 4.89 g of EPON HPT ™ curing agent 1062-M (aromatic diamine available from Shell Chemical Company), and 10.89 g of MY 0510 was prepared and tested. The results are given in table 1.

TABLE 1

Cyanoimide/Epoxy Adhesive Formulations

| | Formulation | | Lap Shear Strength N/mm² | | | | | $T_g$ |
|---|---|---|---|---|---|---|---|---|
| Ex | Polyimide Components | Diluent | RT | 100° C. | 150° C. | 200° C. | 250° C. | (dma) |
| 17 | 6F-DCI + Tactix H41 | 100 wt % MY-0510 | 8 | 7 | 8 | 12 | 5 | char |
| 18 | 6F-DCI + SED-M | 100 wt % EPON 828 | 16 | 18 | 11 | 1 | — | 175° C. |
| 19 | 6F-DCI + 4-DDS | 66 wt % MY-0510 | 10 | — | 11 | 17 | 11 | 240° C. |
| 20 | 6F-DCI + 4-DDS | 100 wt % MY-0510 | 8 | 8 | 10 | 15 | 5 | 264° C. |
| 21 | 6F-DCI + 4-DDS | 150 wt % MY-0510 | 8 | 8 | 9 | 12 | 8 | 240° C. |
| 22 | 6F-DCI + 4-DDS | 75 wt % 1:1 EPON828/MY510 | 8 | 9 | 11 | 13 | 3 | 228° C. |
| 23 | 6F-DCI + 4-DDS | 75 wt % CY-179 | 5 | 5 | 9 | 1 | — | 215° C. |
| 24 | 6F-DCI + 1062-M | 100 wt % MY-0510 | 12 | 13 | 15 | 16 | 6 | 238° C. |

Examples 25 and 26 demonstrate the preparation and curing of compositions comprising a bis-N-cyanoimide, a diamine, and a non-epoxy reactive diluent.

EXAMPLE 25

To a 100 mL 3-necked pyrex resin flask equipped with an overhead stir motor and gas inlet was added 6.0 g of 6F-DCI, 3.13 g of 4-aminophenyl sulfone, and 5.97 g of diethylene glycol dimethacrylate. The mixture was allowed to stir until the components were evenly blended. The stirring rate was reduced, but not stopped, and a vacuum was applied to the system. The resin mixture was allowed to degas for approximately ten minutes. At this point the stirring was stopped, and the reactor brought back to atmospheric pressure. Samples of this resin mixture were cured for 1 h at 180° C. to yield a brittle yellow polymer.

EXAMPLE 26

In the manner described in example 25, an adhesive composition containing 5.61 g of ethoxylated bisphenol A dimethacrylate, 0.06 g of tert-butyl perbenzoate, 6.0 g of 6F-DCI, and 4.89 g of EPON HPT TM curing agent 1062-M (aromatic diamide from Shell Chemical Company) was prepared. Samples of this resin mixture were cured for 1 h at 180° C. to yield a brittle yellow polymer.

Examples 27 through 54 demonstrate the preparation and curing of compositions comprising an epoxy resin and a mono- or polyfunctional N-cyanoimide.

EXAMPLE 27

To a 100 mL 3-necked pyrex resin flask equipped with an overhead stir motor and gas inlet was added 23.0 g of EPON 828 (epoxy equivalent weight $\approx$189), 6.3 g of N-cyanophthalimide (ground and sieved), and 0.6 g of fumed silica. The oxirane to curing agent ratio was 10/3. The mixture was allowed to stir until the components were evenly blended. The stirring rate was reduced, but not stopped, and a vacuum was applied to the system. The resin mixture was allowed to degas for approximately ten minutes. At this point the stirring was stopped, and the reactor brought back to atmospheric pressure.

Samples of resin were cured according to the following five cure schedules:
A = 0.5 h @ 180° C.
B = 0.5 h @ 200° C.
C = 0.5 h @ 220° C.
D = 0.5 h ramp to 180° C., 0.5 h @ 180° C., $\approx$1 h cool down
E = 0.5 h ramp to 125° C., 4.0 h @ 125° C., $\approx$1 h cool down Adhesive performance was evaluated by measuring the tensile lap shear strength of a sample set and the results are given in table 2. The glass transition temperatures ($T_g$) were determined and are given in table 3.

For comparison, a second batch of resin was prepared as described above using an equal molar amount of phthalic anhydride in place of the N-cyanophthalimide. Resin samples were cured according to the cure schedules listed above. Tensile lap shear strengths and glass transition temperatures are given in tables 2 and 3.

EXAMPLE 28

An adhesive composition was prepared and tested as described in example 27 except that 3 wt % of dimethyldistearylammonium chloride (Genamine DSAC) was added as a co-catalyst. Adhesive and thermal properties are given in tables 2 and 3.

EXAMPLE 29

An adhesive composition was prepared and tested as described in example 27 except that 1 wt % of 1-methylimidazole (1-MI) was added as a co-catalyst. Adhesive and thermal properties are given in tables 2 and 3.

EXAMPLE 30

An adhesive composition was prepared and tested as described in example 27 except that 3 wt % of dimethylbenzylamine (DMBA) was added as a co-catalyst. Adhesive and thermal properties are given in tables 2 and 3.

EXAMPLE 31

An adhesive composition was prepared and tested as described in example 27 except that 5 wt % of salicylic acid was added as a co-catalyst. Adhesive and thermal properties are given in tables 2 and 3.

TABLE 2

N-Cyanophthalimide Curing of EPON 828: Adhesive Performance

| Example | Molar Equiv.* | Co-catalyst | Cure Schedules | | | | |
|---|---|---|---|---|---|---|---|
| | | | A | B | C | D | E |
| | | | Room Temperature Lap Shear N/mm² (Anhydride Controls) | | | | |
| 27 | 0.3 | None | 2 | 7 | 10 | 5 | 2 |
| | | | (0) | (6) | (7) | (1) | (0) |
| 28 | 0.3 | 3 wt % Genamine DSAC | 10 | 17 | 18 | 12 | 10 |
| | | | (6) | (5) | (5) | (11) | (9) |
| 29 | 0.3 | 1 wt % 1-MI | 22 | 25 | 20 | 22 | 14 |
| | | | (9) | (14) | (19) | (19) | (18) |
| 30 | 0.3 | 3 wt % DMBA | 17 | 15 | 13 | 18 | 16 |
| | | | (11) | (16) | (16) | (20) | (23) |
| 31 | 0.3 | 5 wt % salicylic acid | 4 | 10 | 14 | 10 | 4 |
| | | | (4) | (12) | (18) | (9) | (4) |
| 32 | 0.3 | 5 wt % Phloroglucinol | 8 | 10 | 12 | 8 | 7 |
| | | | (4) | (11) | (17) | (10) | (9) |
| 33 | 0.3 | 1 wt % TBPB | 11 | 16 | 20 | 16 | 10 |
| | | | (6) | (5) | (5) | (7) | (11) |

*This refers to the stoichiometry between the curing agent and the epoxy, i.e. for every mole of oxirane functionality, there was, for example, 0.3 moles of N-cyanoimide (anhydride) functionality.

EXAMPLE 32

An adhesive composition was prepared and tested as described in example 27 except that 5 wt % of phloroglucinol dihydrate was added as a co-catalyst. Adhesive and thermal properties are given in tables 2 and 3.

EXAMPLE 33

An adhesive composition was prepared and tested as described in example 27 except that 1 wt % of tetrabutylphosphonium bromide (TBPB) was added as a co-catalyst. Adhesive and thermal properties are given in tables 2 and 3.

and 0.44 g of fumed silica. The oxirane to curing agent ratio was 10/3. The mixture was allowed to stir until the components were evenly blended. The stirring rate was reduced, but not stopped, and a vacuum was applied to the system. The resin mixture was allowed to degas for a short period of time, approximately ten minutes. At this point the stirring was stopped, and the reactor brought back to atmospheric pressure. Samples of resin were cured according to the following five cure schedules described in example 27.

Adhesive performance was evaluated by measuring the tensile lap shear strength of a sample set and the results are given in table 4. The glass transition tempera-

TABLE 3

N-Cyanophthalimide Curing of EPON 828: Thermal Performance

| Example | Molar Equiv.* | Co-catalyst | Cure Schedules | | | | |
|---|---|---|---|---|---|---|---|
| | | | A | B | C | D | E |
| | | | Glass Transition Temperature (°C.) (Anhydride Controls) | | | | |
| 27 | 0.3 | None | 50 | 92 | 123 | 45 | 46 |
| | | | (NC)** | (NC) | (NC) | (NC) | (NC) |
| 28 | 0.3 | 3 wt % Genamine DSAC | 115 | 121 | 130 | 121 | 109 |
| | | | (49) | (58) | (43) | (58) | (48) |
| 29 | 0.3 | 1 wt % 1-MI | 130 | 136 | 128 | 134 | 150 |
| | | | (60) | (67) | (81) | (81) | (73) |
| 30 | 0.3 | 3 wt % DMBA | 118 | 126 | 120 | 138 | 138 |
| | | | (83) | (90) | (95) | (97) | (108) |
| 31 | 0.3 | 5 wt % salicylic acid | 48 | 102 | 116 | 92 | 66 |
| | | | (60) | (54) | (29) | (50) | (NC) |
| 32 | 0.3 | 5 wt % Phloroglucinol | 110 | 132 | 124 | 133 | 128 |
| | | | (NC) | (NC) | (NC) | (NC) | (NC) |
| 33 | 0.3 | 1 wt % TBPB | 106 | 118 | 114 | 118 | 93 |
| | | | (30) | (52) | (56) | (41) | (34) |

*This refers to the stoichiometry between the curing agent and the epoxy, i.e. for every mole of oxirane functionality, there was, for example, 0.3 moles of N-cyanoimide (anhydride) functionality.
**Not fully cured.

EXAMPLE 34

To a 100 mL 3-necked pyrex resin flask equipped with an overhead stir motor and gas inlet was added 17.2 g of EPON 828, 5.06 g of 1,3-dihydro-1,3-dioxo-5-methyl-2-H-isoindole-2-carbonitrile (N-cyano-4-methylphthalimide, ground and sieved), 0.67 g of dimethyldistearylammonium chloride (Genamine DSAC), tures ($T_g$) were determined and are also given in table 4.

EXAMPLE 35

An adhesive composition was prepared as described in example 34 except that 1,3-dihydro-1,3-dioxo-5-nitro-2H-isoindole-2-carbonitrile (N-cyano-4-nitrophthalimide) was used as the curing agent. Adhesive and thermal properties are given in table 4.

TABLE 4

Substituted N-Cyanophthalimides as Curing Agents for EPON 828

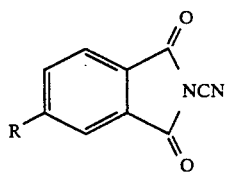

| Example | Molar Equiv.* | Co-catalyst | Cure Schedules | | | | |
|---|---|---|---|---|---|---|---|
| | | | A | B | C | D | E |
| | | | Room Temperature Lap Shear N/mm² | | | | |
| | | | (Glass Transition Temperature °C.) | | | | |
| 28, R=H | 0.3 | 3 wt % Genamine DSAC | 10 | 17 | 18 | 12 | 10 |
| | | | (115) | (121) | (130) | (121) | (109) |
| 34, R=CH₃ | 0.3 | 3 wt % Genamine DSAC | 13 | 14 | 16 | 16 | 14 |
| | | | (125) | (114) | (144) | (130) | (110) |
| 35, R=NO₂ | 0.3 | 3 wt % Genamine DSAC | 14 | 15 | 17 | 18 | 12 |
| | | | (109) | (138) | (147) | (136) | (113) |

*This refers to the stoichiometry between the curing agent and the epoxy, i.e. for every mole of oxirane functionality, there was, for example, 0.3 moles of N-cyanoimide functionality.

EXAMPLE 36

To a 50 mL 3-necked pyrex resin flask equipped with an overhead stir motor and gas inlet was added 25.0 g of EPON 828, 7.00 g of N-cyano-cis-4-cyclohexene-1,2-dicarboximide, 0.96 g of dimethyldistearylammonium chloride (Genamine DSAC), and 0.66 g of fumed silica. The oxirane to curing agent ratio was 10/3. The mixture was allowed to stir until the components were evenly blended. The stirring rate was reduced, but not stopped, and a vacuum was applied to the system. The resin mixture was allowed to degas for a short period of time, approximately ten minutes. At this point the stirring was stopped, and the reactor brought back to atmospheric pressure. Samples of resin were cured according to the following five cure schedules described in example 27.

Adhesive performance was evaluated by measuring the tensile lap shear strength of a sample set and the results are given in table 5. The glass transition temperatures ($T_g$) were determined and are also given in table 5.

EXAMPLE 37-38

Adhesive compositions were prepared and tested as described in example 36 except that 1 wt % of 1-methylimidazole (1-MI), or 3 wt % dimethylbenzylamine (DMBA) were added in place of the dimethyldistearylammonium chloride as co-catalysts. Adhesive and thermal properties are given in table 5.

EXAMPLE 39

To a 100 mL 3-necked pyrex resin flask equipped with an overhead stir motor and gas inlet was added 19.5 g of EPON 828, 3.81 g of 5,5'-[2,2,2-trifluoro-1-(trifluoromethyl)ethylidene]bis(1H-2-cyanoisoindole-1,3(2H)-dione) (6F-DCI), ground and sieved, 0.70 g of dimethyldistearylammonium chloride (Genamine DSAC), and 0.47 g of fumed silica. The oxirane functionality to N-cyanoimide functionality ratio was 10/1.5. The mixture was allowed to stir until the components were evenly blended. The stirring rate was reduced, but not stopped, and a vacuum was applied to the system. The resin mixture was allowed to degas for approximately ten minutes. At this point the stirring was stopped, and the reactor brought back to atmospheric pressure. Samples of resin were cured according to the following five cure schedules described in example 27.

Adhesive performance was evaluated by measuring the tensile lap shear strength of a sample set and the results are given in table 6. The glass transition temperatures ($T_g$) were determined and are also given in table 6

EXAMPLE 40

An adhesive composition was prepared and tested as described in example 39 except that the ratio of oxirane functionality to N-cyanoimide functionality was 10/3. Adhesive and thermal properties are given in table 6.

TABLE 5

N-Cyano-cis-4-cyclohexene-1,2-dicarboximide as Curing Agent for EPON 828

| Example | Molar Equiv.* | Co-catalyst | Cure Schedules | | | | |
|---|---|---|---|---|---|---|---|
| | | | A | B | C | D | E |
| | | | Room Temperature Lap Shear N/mm² | | | | |
| | | | (Glass Transition Temperature °C.) | | | | |
| 36 | 0.3 | 3 wt % Genamine DSAC | 9 (70) | 11 (96) | 15 (109) | 13 (104) | 10 (90) |
| 37 | 0.3 | 1 wt % 1-MI | 17 (C)** | 19 (C) | 21 (C) | 18 (159) | 13 (150) |
| 38 | 0.3 | 3 wt % DMBA | 21 (130) | 20 (136) | 19 (129) | 23 (153) | 16 (140) |

*This refers to the stoichiometry between the curing agent and the epoxy, i.e. for every mole of oxirane functionality, there was, for example, 0.3 moles of N-cyanoimide functionality.
**Charred, samples were unusable due to exothermic reaction during cure.

Examples 41-44

Adhesive compositions were prepared and tested as described in examples 39 and 40 except that 1 wt % of 1-methylimidazole (1-MI), or 3 wt % of dimethylbenzylamine (DMBA) were added in place of the dimethyldistearylammonium chloride as co-catalysts. Adhesive and thermal properties are given in table 6.

TABLE 6

6F-DCI as Curing Agent for EPON 828

| Example | Molar Equiv.* | Co-catalyst | Cure Schedules Room Temperature Lap Shear N/mm² (Glass Transition Temperature °C.) | | | | |
|---|---|---|---|---|---|---|---|
| | | | A | B | C | D | E |
| 39 | 0.15 | 3 wt % Genamine DSAC | 6 (75) | 7 (75) | 9 (85) | 9 (75) | 5 (62) |
| 40 | 0.3 | 3 wt % Genamine DSAC | 9 (131) | 10 (140) | 12 (150) | 15 (133) | 11 (122) |
| 41 | 0.15 | 1 wt % 1-MI | 12 (94) | 19 (127) | 20 (135) | 15 (115) | 13 (120) |
| 42 | 0.3 | 1 wt % 1-MI | 10 (171) | 10 (161) | 20 (161) | 16 (171) | 10 (145) |
| 43 | 0.15 | 3 wt % DMBA | 20 (116) | 19 (133) | 23 (138) | 23 (132) | 15 (149) |
| 44 | 0.3 | 3 wt % DMBA | 12 (157) | 14 (166) | 16 (157) | 19 (167) | 13 (165) |

*This refers to the stoichiometry between the curing agent and the epoxy, i.e. for every mole of oxirane functionality, there was, for example, 0.3 moles of N-cyanoimide functionality.

EXAMPLE 45

To a 100 mL 3-necked pyrex resin flask equipped with an overhead stir motor and gas inlet was added 18.1 g of MY 0510 (epoxy equivalent weight $\approx 101$), 6.45 g of N-cyanophthalimide (ground and sieved), and 0.45 g of fumed silica. The curing agent to oxirane ratio was approximately 1/5. The mixture was allowed to stir until the components were evenly blended. The stirring rate was reduced, but not stopped, and a vacuum was applied to the system. The resin mixture was allowed to degas for approximately ten minutes. At this point the stirring was stopped, and the reactor brought back to atmospheric pressure.

Samples of resin were cured according to the following five cure schedules:
A = 0.5 h @180° C.
B = 0.5 h @200° C.
C = 0.5 h @220° C.

Adhesive and thermal properties are given in table 7.

TABLE 7

N-Cyanophthalimide Curing of Additional Epoxy Resins

| Example | Resin | Molar Equiv.* | Co-catalyst | Cure Schedules Room Temp. Lap Shear N/mm² (Glass Transition Temperature °C.) | | |
|---|---|---|---|---|---|---|
| | | | | A | B | C |
| 45 | MY 0510 | 0.21 | None | 5 (NC)** | 8 (106) | 10 (C) |
| 46 | MY 0510 | 0.21 | 3 wt % Genamine DSAC | 10 (139) | 10 (160) | 11 (C) |
| 47 | MY 0510 | 0.43 | 3 wt % Genamine DSAC | 6 (233) | 6 (244) | 7 (246) |
| 48 | MY 721 | 0.30 | 3 wt % Genamine DSAC | 10 (211) | 9 (212) | 9 (231) |
| 49 | D.E.N. 431 | 0.30 | 2 wt % Genamine DSAC | 13 (114) | 15 (115) | 18 (117) |
| 50 | D.E.N. 438 | 0.30 | 3 wt % Genamine DSAC | 14 (172) | 14 (165) | 14 (163) |

*This refers to the stoichiometry between the curing agent and the epoxy, i.e. for every mole of oxirane functionality, there was, for example, 0.3 moles of N-cyanoimide functionality.
**Not fully cured.
Charred, samples were unusable due to exothermic reaction during cure.

EXAMPLE 46

An adhesive composition was prepared and tested as described in example 45 except that aluminum oxide (equal to the weight of MY 0510 used) was added as filler, and that 3 wt % of dimethyldistearylammonium chloride (Genamine DSAC was added as a co-catalyst. Adhesive and thermal properties are given in table 7.

EXAMPLE 47

An adhesive composition was prepared and tested as described in example 46 except that the curing agent to oxirane ratio was approximately doubled. Adhesive and thermal properties are given in table 7.

EXAMPLE 48

An adhesive composition containing 8.00 g of MY 721 (epoxy equivalent weight $\approx 112$), 3.69 g of N-cyanophthalimide, 0.35 g of dimethyldistearylammonium chloride (Genamine DSAC), and 0.21 g of fumed silica was prepared and tested as described in example 45. Adhesive and thermal properties are given in table 7.

EXAMPLE 49

An adhesive composition containing 22.05 g of D.E.N. 431 (epoxy equivalent weight≈175), 6.49 g of N-cyanophthalimide, 0.9 g of dimethyldistearylammonium chloride (Genamine DSAC), and 0.6 g of fumed silica was prepared and tested as described in example 45. Adhesive and thermal properties are given in table 7.

EXAMPLE 50

To a 100 mL 3-necked jacketed pyrex resin flask equipped with an overhead stir motor and gas inlet was added 8.00 g D.E.N. 438 (epoxy equivalent weight ≈178), 2.32 g of N-cyanophthalimide, 0.31 g of Genamine DSAC, and 0.21 g of fumed silica. The reaction flask was warmed to 50° C. while the mixture was allowed to stir until the components were evenly blended. After degassing, the resin mixture was tested as described in example 45. Adhesive and thermal properties are given in table 7.

EXAMPLE 51

To a 100 mL 3-necked pyrex resin flask equipped with an overhead stir motor and gas inlet was added 4.00 g of MY 0510, and 6.00 g of 5,5'-[2,2,2trifluoro-1-(trifluoromethyl)ethylidene]bis(1H-2-cyanoisoindole-1,3(2H)-dione) (6F-DCI), ground and sieved. The mixture was allowed to stir until the components were evenly blended. The stirring was reduced, but not stopped, and a vacuum was applied to the system. The resin mixture was allowed to degas for approximately ten minutes. At this point the stirring was stopped, and the reactor brought back to atmospheric pressure. Samples of resin were cured at 180° C. during a 60 minute cure time.

Adhesive performance was evaluated by measuring the tensile lap shear strength of a sample set tested at one or more of the following temperatures: room temperature, 100° C., 125° C., 150° C., 200° C., 250° C. Adhesive and thermal properties are given in table 8.

EXAMPLE 52

An adhesive composition containing 8.16 g of EPON 828, 5.44 g of MY 721, 2.00 g of N-cyanophthalimide, 0.40 g 1-methylimidazole, and 8.00 g of aluminum oxide was prepared and tested as described in example 51. Samples of resin were cured at 180° C. during a 30 minute cure time. Adhesive and thermal properties are given in table 8.

TABLE 8

| N-Cyanoimides in High Temperature Adhesive Formulations | | | | | | | |
|---|---|---|---|---|---|---|---|
| Example | Lap Shear Strength N/mm² | | | | | | Tg (DMA) |
| | RT | 100° C. | 125° C. | 150° C. | 200° C. | 250° C. | |
| 51 | 6 | NT* | NT | 6 | 7 | 6 | 283° C. |
| 52 | 16 | 20 | 23 | 21 | 3 | NT | 188° C. |
| 53 | 18 | 19 | 18 | 18 | 8 | NT | 181° C. |
| 54 | 23 | 24 | 22 | 16 | 2 | NT | 138° C. |

*Not tested at this temperature.

EXAMPLE 53

An adhesive composition containing 6.12 g of MY 721, 4.08 g of XU 71790.04 (epoxy equivalent weight ≈292), 1.50 g of N-cyanophthalimide, 0.30 g of 1-methylimidazole, and 6.00 g of aluminum oxide was prepared and tested as described in example 52. Adhesive and thermal properties are given in table 8.

EXAMPLE 54

An adhesive composition containing 4.08 g of MY 0510, 6.12 g of XU 71790.04, 1.50 g of N-cyanophthalimide, 0.30 g of 1-methylimidazole, and 6.00 g of aluminum oxide was prepared and tested as described in example 52. Adhesive and thermal properties are given in table 8.

Examples 55 through 57 demonstrate the reaction of aliphatic N-cyanoimides with aniline to form amide-cyanoamides and the conversion of those products to substituted imides.

EXAMPLE 55

Reaction of N-Cyano-cis-4-cyclohexene-1,2-dicarboximide with Aniline

To a solution of N-cyano-cis-4-cyclohexene-1,2-dicarboximide in THF was added three molar equivalents of aniline, and the resulting mixture was allowed to stir at room temperature for approximately 5 h. The reaction mixture was partitioned between ethyl acetate and 2N hydrochloric acid. The organic phase was washed with brine, dried (MgSO4), and concentrated using a rotary evaporator. Analysis of the crude product reveals a 3:1 mixture of the diamide and imide compounds shown below.

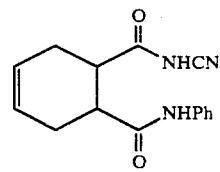

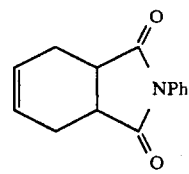

EXAMPLE 56

Preparation and Thermal Behavior of N-Butyl-N'-cyanobutanediamide

To a solution of N-cyanosuccinimide (0.20 g, 1.61 mmol) in 5 mL of THF was added and excess of n-butylamine (0.5 mL, 5.06 mmol), and the resulting mixture was allowed to stir at room temperature for 1 h. The mixture was transferred to a separatory funnel and partitioned between ethyl acetate and 2N hydrochloric acid. The organic phase was washed with brine, dried (MgSO4), and concentrated to give 0.27 g (85%) of a white solid. Analysis of the spectroscopic properties of this material was consistent with the diamide structure shown below.

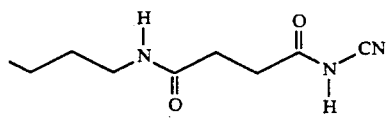

When a sample of this material was analyzed by GC/MS the observed major volatile component was identified as N-butylsuccinimide.

An additional sample, ≈50 mg, was heated to 150° C. for 10 minutes. Analysis of the resulting dark mixture by NMR suggests a blend mostly containing N-butylsuccinimide and the starting diamide.

Analysis of the diamide by DSC shows a well defined melting endotherm at 120° C., followed by an exothermic reaction, exothermic maximum at 125° C. A second scan exhibits no residual reactivity up to 200° C.

EXAMPLE 57

Preparation and Thermal Behavior of N-Cyano-N'-phenylbutanediamide

To a solution of N-cyanosuccinimide (0.19 g, 1.53 mmol) in 5 mL of THF was added an excess of aniline (0.3 mL, 3.3 mmol), and two drops of hexadecane (internal standard). The reaction was allowed to stir at room temperature for 6 h during which time a precipitate was formed. The mixture was transferred to a separatory funnel and partitioned between ethyl acetate and 2N hydrochloric acid. The precipitate remained undissolved. The organic/particulate phase was washed with water, the saturated sodium bicarbonate solution, at which time the suspended solids dissolved. The sodium bicarbonate containing solution was acidified with hydrochloric acid and the resulting precipitate was isolated by filtration and dried under vacuum to yield 0.23 g (70%) of a white powder. Analysis of the spectroscopic properties of this material was consistent with the structure shown below.

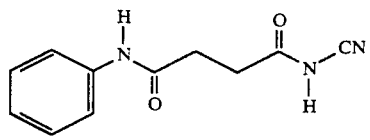

When a sample of this material was analyzed by GC/MS or GC/IR, a single peak identified as N-phenylsuccinimide was observed.

Using high temperature NMR techniques (150° C., nitrobenzene), the rapid conversion of the diamide to N-phenylsuccinimide was observed.

Examples 58 through 73 demonstrate the preparation of poly(amide-cyanoamides) from bis-N-cyanoimides and diamines.

EXAMPLE 58

Equal molar quantities of N,N'-dicyano-1,2,3,4-cyclobutanetetracarboximide and 1,4-diaminobenzene are combined in a N-methylpyrrolidinone (NMP) solution and allowed to stir for 1 h. The poly(amide-cyanoamide) is isolated by precipitation using methanol as the non-solvent. Residual solvent is removed under vacuum to afford a compound of formula V

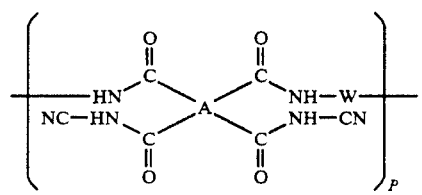

wherein A is cyclobutane moiety, W is a 1,4 substituted benzene moiety, and P is an integer greater than 1.

EXAMPLES 59 THROUGH 73

The procedure of Example 58 is repeated using the bis(N-cyanoimides) and diamines shown in Table 9.

TABLE 9

| Example | Bis-N-cyanoimide | Diamine |
|---|---|---|
| 59 | N,N'-dicyano-3,3',4,4'-biscyclohexyltetracarboximide | 4-aminophenyl ether |
| 60 | same as example 59 | di(4-aminophenyl)methane |
| 61 | same as example 59 | 3-aminophenyl sulfone |
| 62 | same as example 59 | 4-aminophenyl sulfone |
| 63 | same as example 59 | 2,2-bis[(4-aminophenoxy)phenyl]propane |
| 64 | same as example 59 | bis[(3-aminophenoxy)phenyl] sulfone |
| 65 | same as example 59 | EPON HPT 1061-M aromatic diamine |
| 66 | same as example 59 | 1,6-diaminohexane |
| 67 | same as example 59 | isophorone diamine |
| 68 | same as example 59 | trimethylhexamethylene diamine |
| 69 | same as example 59 | triethylene glycol diamine |
| 70 | 4,4'-oxybis(N-cyanocyclohexane-1,2-dicarboximide) | same as example 63 |
| 71 | 4,4'-methylenebis(N-cyanocyclohexane,1,2-dicarboximide) | same as example 69 |
| 72 | 2,2-bis(N-cyanocyclohex-4-yl,1,2-dicarboximide)-1,1,1,3,3,3-hexafluoropropane | same as example 61 |
| 73 | 2,2-bis(N-cyanocyclohex-4-yl-1,2-dicarboximide)propane | same as example 65 |

EXAMPLE 74

A solution of the poly(aminde-cyanoamide) from example 58 in NMP is heated to 150° C. for 1 h. The solution is cooled to room temperature and the resulting polyimide is isolated by precipitation into methanol followed by filtration. The residual solvent is removed under vacuum to afford a compound with the structure given below.

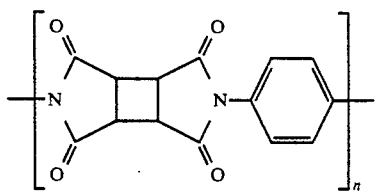

EXAMPLE 75

The procedure of Example 74 is repeated using the poly(amide-cyanoamide) prepared in Example 59 to afford a compound with the structure shown below.

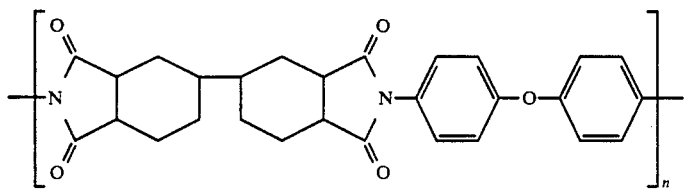

Examples 76 through 78 demonstrate the preparation of a polyimide from a poly(amide-cyanoamide) in the absence of a solvent.

EXAMPLE 76

The poly(amide-cyanoamide) of Example 72 is dissolved in THF and the solution is used to cast a thin film from which the solvent is removed by evaporation. The film of poly(amide-cyanoamide) is cut to size and placed between two aluminum coupons. The specimen is cured in an oven at 180° C. for one hour.

EXAMPLE 77

The poly(amide-cyanoamide) of Example 67 is dissolved in THF and the solution is used to coat carbon fibers after which the solvent is removed by evaporation. The coated fibers are fabricated as uni-directional prepreg into a multi-layer composite which is then cured at 180° C. for 2 hours.

EXAMPLE 78

The poly(amide-cyanoamide) of Example 65 is ground into powder form and is then electrostatically deposited as a powder on a clean steel surface. The powder coating is cured at 180° C. for 2 hours.

Examples 79 through 83 demonstrate the preparation and curing of formulations based on poly(amide-cyanoamides) plus epoxy resins as a reactive diluent and, optionally, other modifiers.

EXAMPLE 79

To a 100 ml 3-necked flask equipped with an overhead stir motor and gas inlet is added 16 grams of the poly(amide-cyanoamide) of Example 69 and 4 grams of MY-0510 epoxy resin. The mixture is allowed to stir until the components are evenly blended and the stirring resin mixture is then degassed under a vacuum for 10 minutes. (Heating is optionally used to facilitate the blending if the mixture is too viscous or requires melting.) At this point the stirring is stopped and the flask is brought back to atmospheric pressure. Samples of the mixture are cured for one hour at 180° C. to yield a hard polymer. An additional sample of the mixture is spread between two aluminum coupons and the specimen is then cured for one hour at 180° C. to yield an adhesively bonded material. A further sample of the mixture is combined with an equal weight of chopped fiber glass and placed in a small mold. The reinforced mixture is cured in a heated press for 2 hours at 220° C. to yield a cured reinforced polymer.

EXAMPLE 80

The procedure of Example 79 is repeated using 4 grams of the poly(amide-cyanoamide) of Example 62 and 16 grams of MY-721 epoxy resin.

EXAMPLE 81

The procedure of Example 79 is repeated using 8 grams of the poly(amide-cyanoamide) of Example 66 plus 8 grams of Epon 828 epoxy resin.

EXAMPLE 82

The procedure of Example 79 is repeated using 16 grams of the poly(amide-cyanoamide) of Example 61 plus 4 grams of XU-71790, a rubber modified epoxy resin.

EXAMPLE 83

The procedure of Example 79 is repeated using 4 grams of the poly(amide-cyanoamide) of Example 70 plus 8 grams of Epon 828 and 8 grams of Aro-Cy B-30, a partially trimerized cyanate ester resin based on bisphenol A and available from Hi-Tek Polymers, Inc.

Examples 84 through 87 demonstrate the preparation and curing of formulations based on poly(amide-cyanoamides) and reactive diluents other than epoxy resins.

EXAMPLE 84

The procedure of Example 79 is repeated using 16 grams of the poly(amide-cyanoamide) of Example 63 plus 4 grams of ethoxylated bisphenol A dimethacrylate.

EXAMPLE 85

The procedure of Example 79 is repeated using 4 grams of the poly(amide-cyanoamide) of Example 60 plus 8 grams of Compimide 353, a commercial mixture of bismaleimides available from Shell Chemical, and 8 grams of diallyl bisphenol A.

EXAMPLE 86

The procedure of Example 79 is repeated using 8 grams of the poly(amide-cyanoamide) of Example 68 plus 8 grams of AroCy B-30, a partially trimerized cyanate ester resin based on bisphenol A and available from Hi-Tek Polymers, Inc.

EXAMPLE 87

The procedure of Example 79 is repeated using 16 grams of the poly(amide-cyanoamide) of Example 64 plus 3 grams of N-vinyl-pyrrolidinone and 1 gram of divinylbenzene.

Examples 88 through 94 demonstrate the synthesis of cycloaliphatic dianhydrides, and their use in polyimide synthesis.

EXAMPLE 88

Preparation of Tetramethyl Oxydi(cyclohexane-3,4-dicarboxylate)

A 1-L stainless steel autoclave was charged with 100 g of oxydi(3,4-dicarbomethoxybenzene), 3.00 g of 5% rhodium on alumina, and 750 mL of THF. With stirring, the reactor was purged several times with hydrogen and then charged to approximately 2000 psi of hydrogen. The reaction mixture was heated to 120° C., and the mixture was allowed to stir for 20 h. The reactor was cooled and vented, and the crude reaction mixture removed. The solution was filtered to remove catalyst and then concentrated using a rotary evaporator. The oily residue was partitioned between water and ethyl acetate. The organic phase was washed with brine, dried (MgSO$_4$), and concentrated to a clear lightly colored oil using a rotary evaporator. Gas chromatographic analysis of the crude product reveals a mixture of tetramethyl oxydi(cyclohexane-3,4-dicarboxylate) (major), dimethyl cyclohexanedicarboxylate (minor), and dimethyl 4-hydroxycyclohexanedicarboxylate (minor).

The combined product mixtures of several such runs were purified by Wipe-Film evaporation. To a 2" Pope Wipe-Film distillation apparatus was added approximately 350 g of crude tetramethyl oxydi(cyclohexane-3,4-dicarboxylate) over a 3 h period. The column temperature was held at 130° C. and a vacuum of 100-400 millitorr was applied. A light brown residue was collected, approximately 270 g, which became a viscous glass on cooling. Analysis of the spectroscopic properties of this material was consistent with the biscyclohexyl ether shown below.

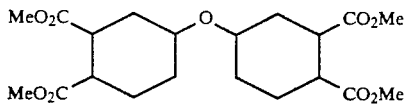

EXAMPLE 89

A 250 mL round-bottomed flask was charged with 5.20 g of the tetramethyl ester from example 88, 33.75 g of methanol, and 33.75 g of 10% sodium hydroxide solution. The resulting mixture was heated to reflux and allowed to stir for 6 h. The solution was allowed to cool to room temperature. Most of the methanol was removed using a rotary evaporator, and the aqueous solution was acidified to pH 1 using concentrated hydrochloric acid. The solution was stored in a refrigerator at which time a fine white precipitate was formed. The white solid was isolated by filtration and dried to afford 2.35 g of a fine white powder. Analysis of the spectroscopic properties of this material was consistent with the structure shown below.

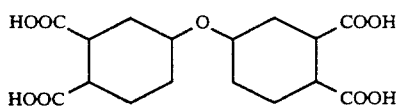

The yield of product may be optionally improved by the following procedure. The filtrate was extracted with tetrahydrofuran, which was then washed with brine. The THF solution was dried (MgSO$_4$) and concentrated to afford a white solid, 1.83 g. This material was also identified as the tetracarboxylic acid shown above.

EXAMPLE 90

A 100 mL round-bottomed flask was charged with 1.40 g of the tetracarboxylic acid prepared in the manner described in example 89, and 20 mL of acetic anhydride. The resulting mixture was heated to reflux and allowed to stir for 3 h. The mixture was concentrated using a rotary evaporator, and residual acetic anhydride was removed under vacuum to afford 0.74 g of a viscous oil. Spectroscopic analysis of this material was consistent with the dianhydride structure shown below.

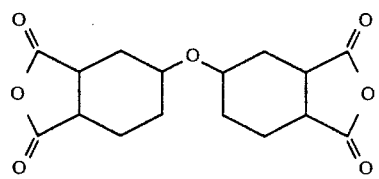

EXAMPLE 91

Hydrogenation of oxydi(3,4-dicarbomethoxybenzene) Using Ruthenium

A 300 mL stainless steel autoclave was charged with 6.0 g of oxydi(3,4-dicarbomethoxybenzene), 2.00 g of 5% ruthenium on carbon (50% water), and 100 mL of a 1% solution of acetic acid in methanol. With stirring, the reactor was purged several times with hydrogen, then charge to approximately 2000 psi of hydrogen. The reaction mixture was heated to 120° C., and the mixture was allowed to stir for approximately 16 h. The reactor was cooled and vented, and the crude reaction mixture removed. The solution was filtered to remove catalyst, and then concentrated using a rotary evaporator. The oily residue was partitioned between water and ethyl acetate. The organic phase was washed with brine, dried (MgSO$_4$), and concentrated to a clear colorless oil using a rotary evaporator. Gas chromatographic analysis of the crude product revealed a mixture of dimethyl cyclohexane-1,2-dicarboxylate, dimethyl 4-hydroxycyclohexane-1,2-dicarboxylate, tetramethyl oxydi(cyclohexane-3,4-dicarboxylate), and a trace of starting material.

EXAMPLE 92

Hydrogenation of 2,2-bis[(3,4-dicarbomethoxy)phenyl]-1,1,1,3,3,3-hexafluoropropane A 300 mL stainless steel autoclave was charged with 10.0 g of 2,2-bis[(3,4-dicarbomethoxy)phenyl]-1,1,1,3,3,3-hexafluoropropane, 2.00 g of 5% rhodium on alumina, and 100 mL of a 1% solution of acetic acid in methanol. With stirring, the reactor was purged several times with hydrogen and then charged to approximately 3500 psi of hydrogen. The reaction mixture was heated to 150° C., and the mixture was allowed to stir for approximately 48 h. The reactor was cooled and vented, and the crude reaction mixture removed. The solution was filtered to remove catalyst and then concentrated using a rotary evaporator. The oily residue was partitioned between water and ethyl acetate. The organic phase was washed with brine, dried (MgSO$_4$), and concentrated to a clear colorless oil using a rotary evaporator. Gas chromatographic analysis of the crude product revealed a mixture of starting material (minor), and both the dicyclohexyl and mono-cyclohexyl-monoaromatic compounds shown below.

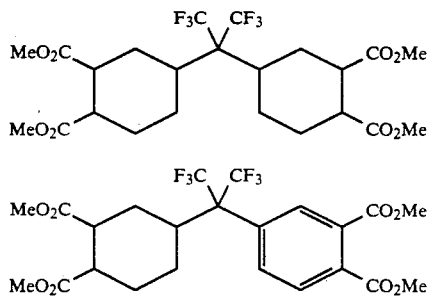

EXAMPLE 93

A 1000 mL stainless steel autoclave was charged with 5.0 g of di(3,4-carbomethoxyphenyl)carbinol, 1.75 g of 5% rhodium on alumina, and 200 mL of a 1% solution of acetic acid in methanol. With stirring, the reactor was purged several times with hydrogen and then charged to approximately 2000 psi of hydrogen. The reaction mixture was heated to 120° C., and the mixture was allowed to stir for approximately 4 h. The reactor was cooled and vented, and the crude reaction mixture removed. The solution was filtered to remove catalyst and then concentrated using a rotary evaporator. The oily residue was partitioned between water and ethyl acetate. The organic phase was washed with brine, dried (MgSO$_4$), and concentrated to a clear colorless oil using a rotary evaporator. Gas chromatographic analysis of the crude product revealed 4,4'-methylenebis(1,2-carbomethoxycyclohexane) as a major component of the product mixture.

EXAMPLE 94

To a 500 mL round-bottomed flask was added 3.86 g of 5,5'-oxybis(hexahydro-1,3-isobenzofurandione (from example 90), 4.91 g of 2,2-bis[(4-aminophenoxy)-phenyl]propane (BAPP), 100 g of N-methylpyrrolidinone, and 25 g of N-cyclohexylpyrrolidinone. The resulting solution was allowed to stir at room temperature for 72 h. The solution was heated to approximately 200° C. and allowed to stir for 24 h. The solution was allowed to cool, the resulting polymer was precipitated into 2 liters of rapidly stirring methanol. The white powder was washed twice with fresh methanol and then dried under vacuum. This afforded 5.92 g (71%) of a fine white powder. A glass transition temperature of 159° C. (DSC) was observed. Analysis of the spectroscopic properties of this material was consistent with the polymeric structure shown below.

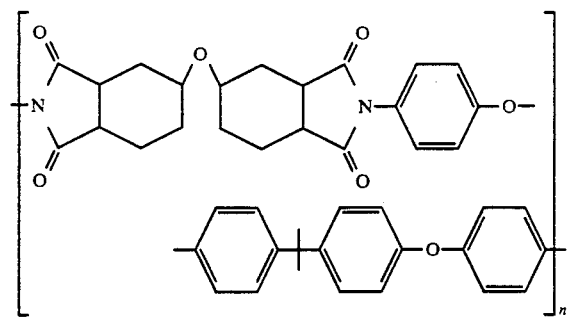

EXAMPLE 95

A 1000 mL stainless steel autoclave was charged with 2.0 g of di(3,4-carbomethoxyphenyl)carbinol, 1.00 g of 5% rhodium on alumina, and 250 mL of THF. With stirring, the reactor was purged several times with hydrogen and then charged to approximately 2000 psi of hydrogen. The reaction mixture was heated to 120° C., and the mixture was allowed to stir for approximately 20 h. The reactor was cooled and vented, and the crude reaction mixture removed. The solution was filtered to remove catalyst and then concentrated using a rotary evaporator. The oily residue was partitioned between water and ethyl acetate. The organic phase was washed with brine, dried (MgSO$_4$), and concentrated to a clear colorless oil using a rotary evaporator. The product was identified as a mixture of di(3,4-carbomethoxycyclohexyl)carbinol (major) and 4,4'-methylenebis-(1,2-carbomethoxycyclohexane) (minor).

What is claimed is:

1. A poly-N-cyanoimide selected from the group consisting of the following:

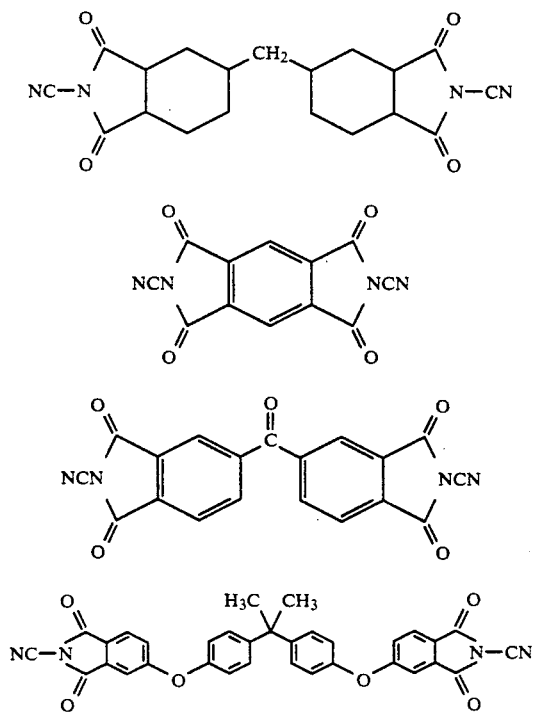

-continued
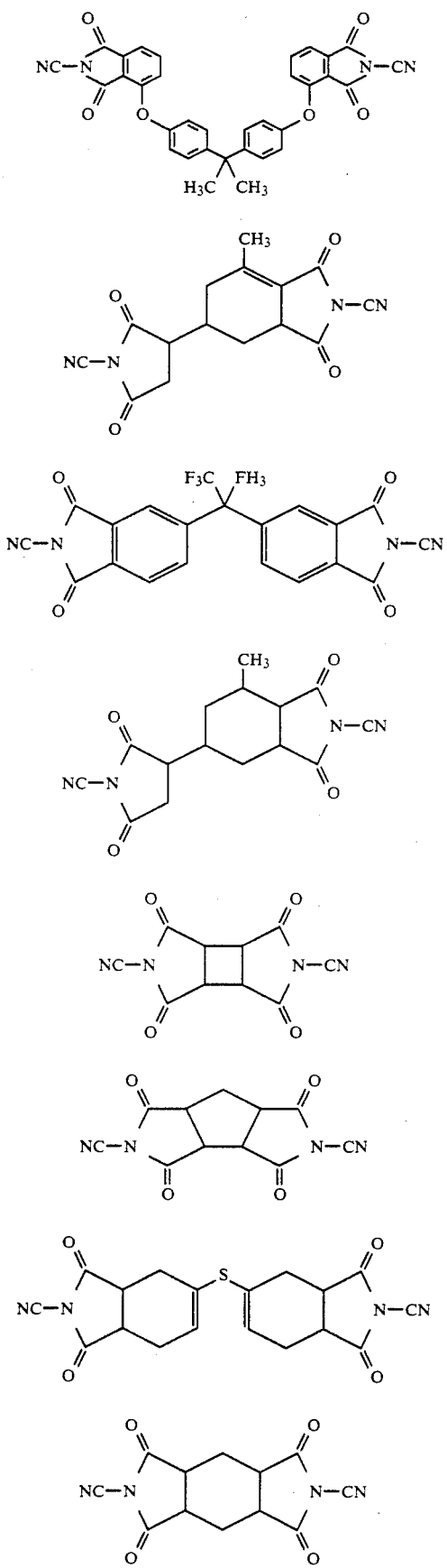
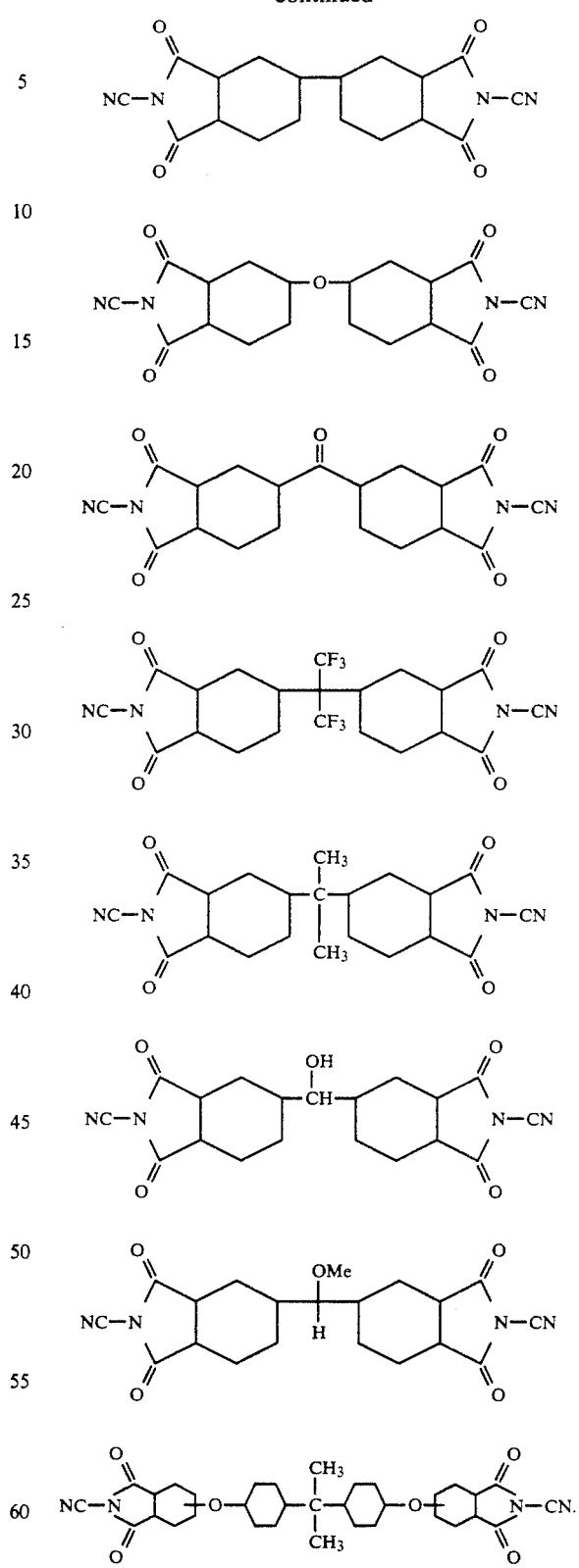
2. The poly-N-cyanoimide of claim 1 wherein the poly-N-cyanoimide has the following structure:

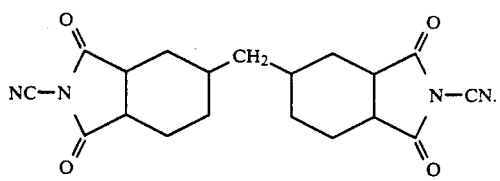

3. The poly-N-cyanoimide of claim 1 wherein the poly-N-cyanoimide has the following structure:

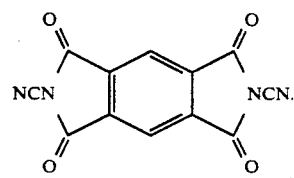

4. The poly-N-cyanoimide of claim 1 wherein the poly-N-cyanoimide has the following structure:

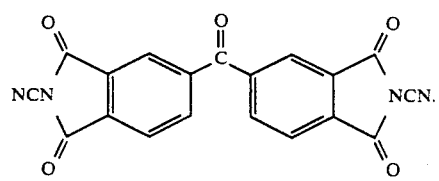

5. The poly-N-cyanoimide of claim 1 wherein the poly-N-cyanoimide has the following structure:

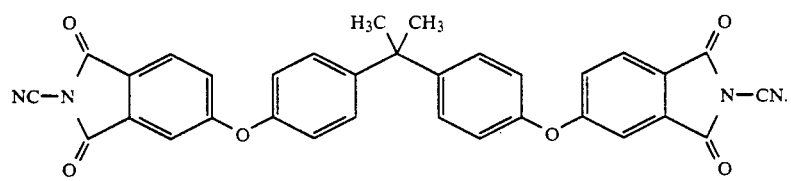

6. The poly-N-cyanoimide of claim 1 wherein the poly-N-cyanoimide has the following structure:

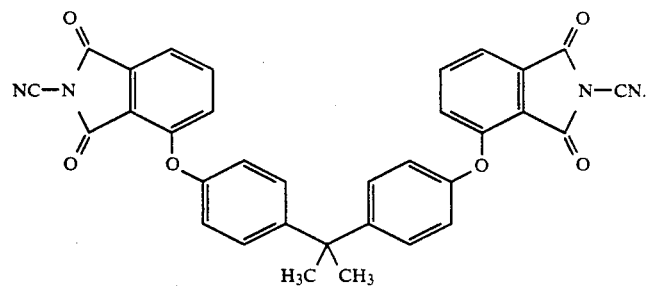

7. The poly-N-cyanoimide of claim 1 wherein the poly-N-cyanoimide has the following structure:

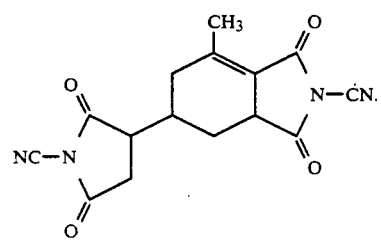

8. The poly-N-cyanoimide of claim 1 wherein the poly-N-cyanoimide has the following structure:

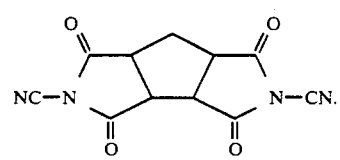

9. The poly-N-cyanoimide of claim 1 wherein the poly-N-cyanoimide has the following structure:

10. The poly-N-cyanoimide of claim 1 wherein the poly-N-cyanoimide has the following structure:

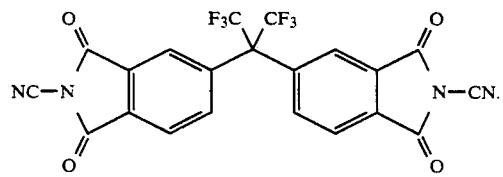

11. The poly-N-cyanoimide of claim 1 wherein the poly-N-cyanoimide has the following structure:

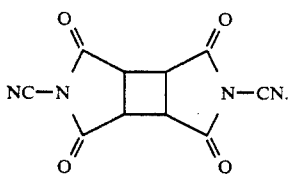

12. The poly-N-cyanoimide of claim 1 wherein the poly-N-cyanoimide has the following structure:

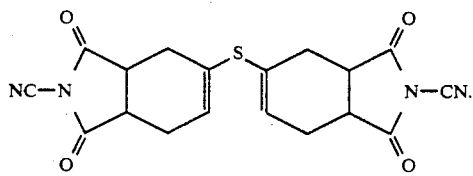

13. The poly-N-cyanoimide of claim 1 wherein the poly-N-cyanoimide has the following structure:

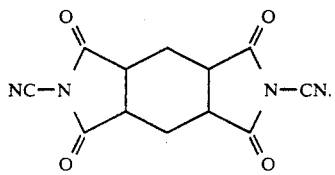

14. The poly-N-cyanoimide of claim 1 wherein the poly-N-cyanoimide has the following structure:

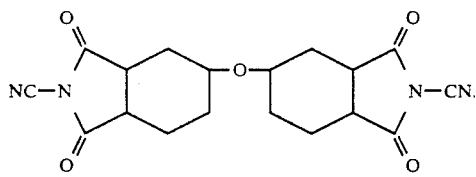

15. The poly-N-cyanoimide of claim 1 wherein the poly-N-cyanoimide has the following structure:

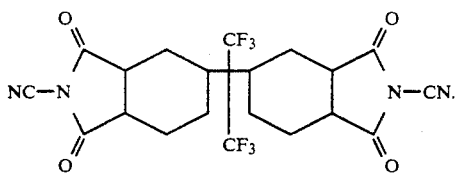

16. The poly-N-cyanoimide of claim 1 wherein the poly-cyanoimide has the following structure:

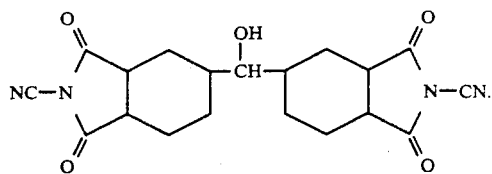

17. The poly-N-cyanoimide of claim 1 wherein the poly-N-cyanoimide has the following structure:

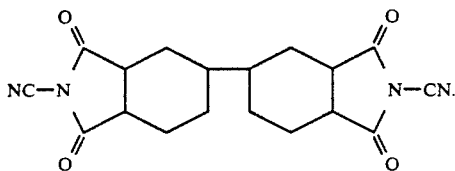

18. The poly-N-cyanoimide of claim 1 wherein the poly-N-cyanoimide has the following structure:

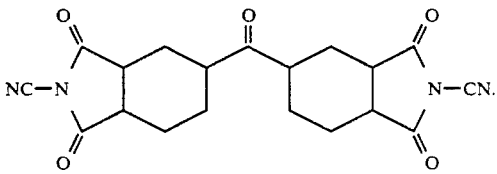

19. The poly-N-cyanoimide of claim 1 wherein the poly-N-cyanoimide has the following structure:

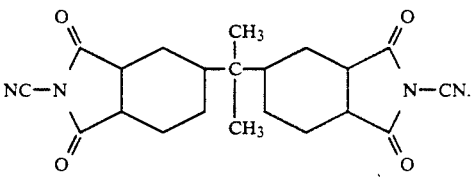

20. The poly-N-cyanoimide of claim 1 wherein the poly-N-cyanoimide has the following structure:

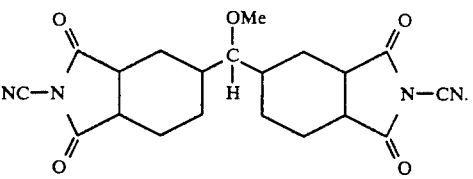

21. The poly-N-cyanoimide of claim 1 wherein the poly-N-cyanoimide has the following structure:

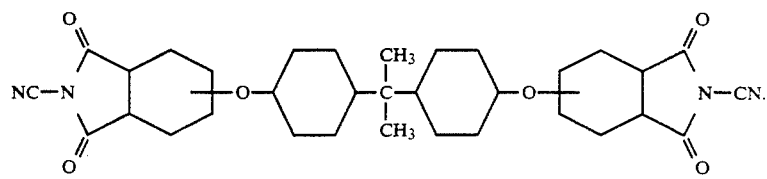

* * * * *